(12) United States Patent
Saadat et al.

(10) Patent No.: US 8,694,071 B2
(45) Date of Patent: Apr. 8, 2014

(54) IMAGE STABILIZATION TECHNIQUES AND METHODS

(75) Inventors: Vahid Saadat, Atherton, CA (US); Michael J. Drews, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/025,981

(22) Filed: Feb. 11, 2011

(65) Prior Publication Data

US 2012/0016221 A1    Jan. 19, 2012

Related U.S. Application Data

(60) Provisional application No. 61/304,235, filed on Feb. 12, 2010.

(51) Int. Cl.
*A61B 5/05* (2006.01)

(52) U.S. Cl.
USPC .......................................... 600/407; 600/479

(58) Field of Classification Search
None
See application file for complete search history.

(56) References Cited

U.S. PATENT DOCUMENTS

| | | |
|---|---|---|
| 623,022 A | 4/1899 | Johnson |
| 2,305,462 A | 12/1942 | Wolf |
| 2,453,862 A | 11/1948 | Peter |
| 3,559,651 A | 2/1971 | Moss |
| 3,874,388 A | 4/1975 | King et al. |
| 3,903,877 A | 9/1975 | Terada |
| 4,175,545 A | 11/1979 | Termanini |
| 4,326,529 A | 4/1982 | Doss et al. |
| 4,445,892 A | 5/1984 | Hussein et al. |
| 4,470,407 A | 9/1984 | Hussein et al. |
| 4,517,976 A | 5/1985 | Murakoshi et al. |
| 4,569,335 A | 2/1986 | Tsuno |
| 4,576,146 A | 3/1986 | Kawazoe et al. |
| 4,615,333 A | 10/1986 | Taguchi |
| 4,619,247 A | 10/1986 | Inoue et al. |
| 4,676,258 A | 6/1987 | Inokuchi et al. |
| 4,681,093 A | 7/1987 | Ono et al. |
| 4,709,698 A | 12/1987 | Johnston et al. |

(Continued)

FOREIGN PATENT DOCUMENTS

| | | |
|---|---|---|
| DE | 10028155 A1 | 12/2000 |
| EP | 0283661 | 9/1988 |

(Continued)

OTHER PUBLICATIONS

Avitall, "A Catheter System to Ablate Atrial Fibrillation in a Sterile Pericarditis Dog Model", *PACE*, vol. 17, p. 774, 1994.

(Continued)

*Primary Examiner* — Long V. Le
*Assistant Examiner* — Nicholas Evoy
(74) *Attorney, Agent, or Firm* — Haynes and Boone, LLP

(57) ABSTRACT

Direct optical imaging of anatomical features and structures from within a biological organ in a dynamic environment (where the tissue being imaged is in motion due to cardiac rhythms, respiration, etc) presents certain image stability issues due (and/or related) to the motion of the target structure and may limit the ability of the user to visually interpret the image for the purposes of diagnostics and therapeutics. Systems and mechanisms for the purpose of actively stabilizing the image or for compiling and re-displaying the image information in a manner that is more suitable to interpretation by the user are disclosed.

10 Claims, 22 Drawing Sheets

(56) References Cited

U.S. PATENT DOCUMENTS

| | | |
|---|---|---|
| 4,710,192 A | 12/1987 | Liotta et al. |
| 4,727,418 A | 2/1988 | Kato et al. |
| 4,784,133 A | 11/1988 | Mackin |
| 4,838,246 A | 6/1989 | Hahn et al. |
| 4,848,323 A | 7/1989 | Marijnissen et al. |
| 4,911,148 A | 3/1990 | Sosnowski et al. |
| 4,914,521 A | 4/1990 | Adair |
| 4,943,290 A | 7/1990 | Rexroth et al. |
| 4,950,285 A | 8/1990 | Wilk |
| 4,957,484 A | 9/1990 | Murtfeldt |
| 4,961,738 A | 10/1990 | Mackin |
| 4,976,710 A | 12/1990 | Mackin |
| 4,991,578 A | 2/1991 | Cohen |
| 4,994,069 A | 2/1991 | Ritchart et al. |
| 4,998,916 A | 3/1991 | Hammerslag et al. |
| 4,998,972 A | 3/1991 | Chin et al. |
| 5,047,028 A | 9/1991 | Qian |
| 5,057,106 A | 10/1991 | Kasevich et al. |
| 5,090,959 A | 2/1992 | Samson et al. |
| 5,123,428 A | 6/1992 | Schwarz |
| RE34,002 E | 7/1992 | Adair |
| 5,156,141 A | 10/1992 | Krebs et al. |
| 5,171,259 A | 12/1992 | Inoue |
| 5,281,238 A | 1/1994 | Chin et al. |
| 5,282,827 A | 2/1994 | Kensey et al. |
| 5,306,234 A | 4/1994 | Johnson |
| 5,313,943 A | 5/1994 | Houser et al. |
| 5,330,496 A | 7/1994 | Alferness |
| 5,334,159 A | 8/1994 | Turkel |
| 5,334,193 A | 8/1994 | Nardella |
| 5,336,252 A | 8/1994 | Cohen |
| 5,339,800 A | 8/1994 | Wilta et al. |
| 5,348,554 A | 9/1994 | Imran et al. |
| 5,353,792 A | 10/1994 | Lubbers et al. |
| 5,370,647 A | 12/1994 | Graber et al. |
| 5,373,840 A | 12/1994 | Knighton |
| 5,375,612 A | 12/1994 | Cottenceau et al. |
| 5,385,148 A | 1/1995 | Lesh et al. |
| 5,391,182 A | 2/1995 | Chin |
| 5,403,326 A | 4/1995 | Harrison et al. |
| 5,405,376 A | 4/1995 | Mulier et al. |
| 5,421,338 A | 6/1995 | Crowley et al. |
| 5,431,649 A | 7/1995 | Mulier et al. |
| 5,453,785 A | 9/1995 | Lenhardt et al. |
| 5,462,521 A | 10/1995 | Brucker et al. |
| 5,471,515 A | 11/1995 | Fossum et al. |
| 5,498,230 A | 3/1996 | Adair |
| 5,505,730 A | 4/1996 | Edwards |
| 5,515,853 A | 5/1996 | Smith et al. |
| 5,527,338 A | 6/1996 | Purdy |
| 5,549,603 A | 8/1996 | Feiring |
| 5,558,619 A | 9/1996 | Kami et al. |
| 5,571,088 A | 11/1996 | Lennox et al. |
| 5,575,756 A | 11/1996 | Karasawa et al. |
| 5,575,810 A | 11/1996 | Swanson et al. |
| 5,584,872 A | 12/1996 | LaFontaine et al. |
| 5,591,119 A | 1/1997 | Adair |
| 5,593,422 A | 1/1997 | Muijs Van de Moer et al. |
| 5,593,424 A | 1/1997 | Northrup, III |
| 5,672,153 A | 9/1997 | Lax et al. |
| 5,676,693 A | 10/1997 | LaFontaine |
| 5,681,308 A | 10/1997 | Edwards et al. |
| 5,695,448 A | 12/1997 | Kimura et al. |
| 5,697,281 A | 12/1997 | Eggers et al. |
| 5,697,882 A | 12/1997 | Eggers et al. |
| 5,709,224 A | 1/1998 | Behl et al. |
| 5,713,907 A | 2/1998 | Hogendijk et al. |
| 5,713,946 A | 2/1998 | Ben-Haim |
| 5,716,321 A | 2/1998 | Kerin et al. |
| 5,722,403 A | 3/1998 | McGee et al. |
| 5,725,523 A | 3/1998 | Mueller |
| 5,746,747 A | 5/1998 | McKeating |
| 5,749,846 A | 5/1998 | Edwards et al. |
| 5,749,890 A | 5/1998 | Shaknovich |
| 5,754,313 A | 5/1998 | Pelchy et al. |
| 5,766,137 A | 6/1998 | Omata |
| 5,769,846 A | 6/1998 | Edwards et al. |
| 5,792,045 A | 8/1998 | Adair |
| 5,797,903 A | 8/1998 | Swanson et al. |
| 5,823,947 A | 10/1998 | Yoon et al. |
| 5,827,268 A | 10/1998 | Laufer |
| 5,829,447 A | 11/1998 | Stevens et al. |
| 5,842,973 A | 12/1998 | Bullard |
| 5,843,118 A | 12/1998 | Sepetka et al. |
| 5,848,969 A | 12/1998 | Panescu et al. |
| 5,860,974 A | 1/1999 | Abele |
| 5,860,991 A | 1/1999 | Klein et al. |
| 5,865,791 A | 2/1999 | Whayne et al. |
| 5,873,815 A | 2/1999 | Kerin et al. |
| 5,879,366 A | 3/1999 | Shaw et al. |
| 5,895,417 A | 4/1999 | Pomeranz et al. |
| 5,897,487 A | 4/1999 | Ouchi |
| 5,897,553 A | 4/1999 | Mulier et al. |
| 5,902,328 A | 5/1999 | LaFontaine et al. |
| 5,904,651 A | 5/1999 | Swanson et al. |
| 5,908,445 A | 6/1999 | Whayne et al. |
| 5,925,038 A | 7/1999 | Panescu et al. |
| 5,928,250 A | 7/1999 | Koike et al. |
| 5,929,901 A | 7/1999 | Adair et al. |
| 5,941,845 A | 8/1999 | Tu et al. |
| 5,944,690 A | 8/1999 | Falwell et al. |
| 5,964,755 A | 10/1999 | Edwards |
| 5,968,053 A | 10/1999 | Revelas |
| 5,971,983 A | 10/1999 | Lesh |
| 5,986,693 A | 11/1999 | Adair et al. |
| 5,997,571 A | 12/1999 | Farr et al. |
| 6,004,269 A | 12/1999 | Crowley et al. |
| 6,012,457 A | 1/2000 | Lesh |
| 6,024,740 A | 2/2000 | Lesh et al. |
| 6,027,501 A | 2/2000 | Goble et al. |
| 6,036,685 A | 3/2000 | Mueller |
| 6,043,839 A | 3/2000 | Adair et al. |
| 6,047,218 A | 4/2000 | Whayne et al. |
| 6,063,077 A | 5/2000 | Schaer |
| 6,063,081 A | 5/2000 | Mulier et al. |
| 6,068,653 A | 5/2000 | LaFontaine |
| 6,071,279 A | 6/2000 | Whayne et al. |
| 6,071,302 A | 6/2000 | Sinofsky et al. |
| 6,081,740 A | 6/2000 | Gombrich et al. |
| 6,086,528 A | 7/2000 | Adair |
| 6,086,534 A | 7/2000 | Kesten |
| 6,099,498 A | 8/2000 | Addis |
| 6,099,514 A | 8/2000 | Sharkey et al. |
| 6,102,905 A | 8/2000 | Baxter et al. |
| 6,112,123 A | 8/2000 | Kelleher et al. |
| 6,115,626 A | 9/2000 | Whayne et al. |
| 6,123,703 A | 9/2000 | Tu et al. |
| 6,123,718 A | 9/2000 | Tu et al. |
| 6,129,724 A | 10/2000 | Fleischman et al. |
| 6,139,508 A | 10/2000 | Simpson et al. |
| 6,142,993 A | 11/2000 | Whayne et al. |
| 6,152,144 A | 11/2000 | Lesh et al. |
| 6,156,350 A | 12/2000 | Constantz |
| 6,159,203 A | 12/2000 | Sinofsky |
| 6,161,543 A | 12/2000 | Cox et al. |
| 6,164,283 A | 12/2000 | Lesh |
| 6,167,297 A | 12/2000 | Benaron |
| 6,168,591 B1 | 1/2001 | Sinofsky |
| 6,168,594 B1 | 1/2001 | LaFontaine et al. |
| 6,174,307 B1 | 1/2001 | Daniel et al. |
| 6,178,346 B1 | 1/2001 | Amundson et al. |
| 6,190,381 B1 | 2/2001 | Olsen et al. |
| 6,211,904 B1 | 4/2001 | Adair et al. |
| 6,224,553 B1 | 5/2001 | Nevo |
| 6,231,561 B1 | 5/2001 | Frazier et al. |
| 6,234,995 B1 | 5/2001 | Peacock, III |
| 6,235,044 B1 | 5/2001 | Root et al. |
| 6,237,605 B1 | 5/2001 | Vaska et al. |
| 6,238,393 B1 | 5/2001 | Mulier et al. |
| 6,240,312 B1 | 5/2001 | Alfano et al. |
| 6,254,598 B1 | 7/2001 | Edwards et al. |
| 6,258,083 B1 | 7/2001 | Daniel et al. |
| 6,263,224 B1 | 7/2001 | West |
| 6,270,492 B1 | 8/2001 | Sinofsky |

(56) References Cited

U.S. PATENT DOCUMENTS

| | | |
|---|---|---|
| 6,275,255 B1 | 8/2001 | Adair et al. |
| 6,290,689 B1 | 9/2001 | Delaney et al. |
| 6,306,081 B1 | 10/2001 | Ishikawa et al. |
| 6,310,642 B1 | 10/2001 | Adair et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,777 B1 | 11/2001 | Comben |
| 6,315,778 B1 | 11/2001 | Gambale et al. |
| 6,322,536 B1 | 11/2001 | Rosengart et al. |
| 6,325,797 B1 | 12/2001 | Stewart et al. |
| 6,328,727 B1 | 12/2001 | Frazier et al. |
| 6,358,247 B1 | 3/2002 | Altman et al. |
| 6,358,248 B1 | 3/2002 | Mulier et al. |
| 6,375,654 B1 | 4/2002 | McIntyre |
| 6,379,345 B1 | 4/2002 | Constantz |
| 6,385,476 B1 | 5/2002 | Osadchy et al. |
| 6,387,043 B1 | 5/2002 | Yoon |
| 6,387,071 B1 | 5/2002 | Constantz |
| 6,394,096 B1 | 5/2002 | Constantz |
| 6,396,873 B1 | 5/2002 | Goldstein et al. |
| 6,398,780 B1 | 6/2002 | Farley et al. |
| 6,401,719 B1 | 6/2002 | Farley et al. |
| 6,409,722 B1 | 6/2002 | Hoey et al. |
| 6,416,511 B1 | 7/2002 | Lesh et al. |
| 6,419,669 B1 | 7/2002 | Frazier et al. |
| 6,423,051 B1 | 7/2002 | Kaplan et al. |
| 6,423,055 B1 | 7/2002 | Farr et al. |
| 6,423,058 B1 | 7/2002 | Edwards et al. |
| 6,428,536 B2 | 8/2002 | Panescu et al. |
| 6,436,118 B1 | 8/2002 | Kayan |
| 6,440,061 B1 | 8/2002 | Wenner et al. |
| 6,440,119 B1 | 8/2002 | Nakada et al. |
| 6,458,151 B1 | 10/2002 | Saltiel |
| 6,461,327 B1 | 10/2002 | Addis et al. |
| 6,464,697 B1 | 10/2002 | Edwards et al. |
| 6,474,340 B1 | 11/2002 | Vaska et al. |
| 6,475,223 B1 | 11/2002 | Werp et al. |
| 6,478,769 B1 | 11/2002 | Parker |
| 6,482,162 B1 | 11/2002 | Moore |
| 6,484,727 B1 | 11/2002 | Vaska et al. |
| 6,485,489 B2 | 11/2002 | Teirstein et al. |
| 6,488,671 B1 | 12/2002 | Constantz et al. |
| 6,494,902 B2 | 12/2002 | Hoey et al. |
| 6,497,705 B2 | 12/2002 | Comben |
| 6,500,174 B1 | 12/2002 | Maguire et al. |
| 6,502,576 B1 | 1/2003 | Lesh |
| 6,514,249 B1 | 2/2003 | Maguire et al. |
| 6,517,533 B1 | 2/2003 | Swaminathan |
| 6,527,979 B2 | 3/2003 | Constantz et al. |
| 6,532,380 B1 | 3/2003 | Close et al. |
| 6,533,767 B2 | 3/2003 | Johansson et al. |
| 6,537,272 B2 | 3/2003 | Christopherson et al. |
| 6,540,733 B2 | 4/2003 | Constantz et al. |
| 6,540,744 B2 | 4/2003 | Hassett et al. |
| 6,544,195 B2 | 4/2003 | Wilson et al. |
| 6,547,780 B1 | 4/2003 | Sinofsky |
| 6,558,375 B1 | 5/2003 | Sinofsky et al. |
| 6,558,382 B2 | 5/2003 | Jahns et al. |
| 6,562,020 B1 | 5/2003 | Constantz et al. |
| 6,572,609 B1 | 6/2003 | Farr et al. |
| 6,579,285 B2 | 6/2003 | Sinofsky |
| 6,585,732 B2 | 7/2003 | Mulier et al. |
| 6,587,709 B2 | 7/2003 | Solf et al. |
| 6,593,884 B1 | 7/2003 | Gilboa et al. |
| 6,605,055 B1 | 8/2003 | Sinofsky et al. |
| 6,613,062 B1 | 9/2003 | Leckrone et al. |
| 6,622,732 B2 | 9/2003 | Constantz |
| 6,626,855 B1 | 9/2003 | Weng et al. |
| 6,626,899 B2 | 9/2003 | Houser et al. |
| 6,626,900 B1 | 9/2003 | Sinofsky et al. |
| 6,635,070 B2 | 10/2003 | Evans et al. |
| 6,645,202 B1 | 11/2003 | Pless et al. |
| 6,650,923 B1 | 11/2003 | Lesh et al. |
| 6,658,279 B2 | 12/2003 | Swanson et al. |
| 6,659,940 B2 | 12/2003 | Adler |
| 6,673,090 B2 | 1/2004 | Root et al. |
| 6,676,656 B2 | 1/2004 | Sinofsky |
| 6,679,836 B2 | 1/2004 | Couvillon, Jr. |
| 6,682,526 B1 | 1/2004 | Parker et al. |
| 6,689,128 B2 | 2/2004 | Sliwa, Jr. et al. |
| 6,692,430 B2 | 2/2004 | Adler |
| 6,701,581 B2 | 3/2004 | Senovich et al. |
| 6,701,931 B2 | 3/2004 | Sliwa, Jr. et al. |
| 6,702,780 B1 | 3/2004 | Gilboa et al. |
| 6,704,043 B2 | 3/2004 | Goldstein et al. |
| 6,706,039 B2 | 3/2004 | Mulier et al. |
| 6,712,798 B2 | 3/2004 | Constantz |
| 6,719,747 B2 | 4/2004 | Constantz et al. |
| 6,719,755 B2 | 4/2004 | Sliwa, Jr. et al. |
| 6,730,063 B2 | 5/2004 | Delaney et al. |
| 6,736,810 B2 | 5/2004 | Hoey et al. |
| 6,751,492 B2 | 6/2004 | Ben-Haim |
| 6,755,790 B2 | 6/2004 | Stewart et al. |
| 6,755,811 B1 | 6/2004 | Constantz |
| 6,764,487 B2 | 7/2004 | Mulier et al. |
| 6,771,996 B2 | 8/2004 | Bowe et al. |
| 6,773,402 B2 | 8/2004 | Govari et al. |
| 6,780,151 B2 | 8/2004 | Grabover et al. |
| 6,805,128 B1 | 10/2004 | Pless et al. |
| 6,805,129 B1 | 10/2004 | Pless et al. |
| 6,811,562 B1 | 11/2004 | Pless |
| 6,833,814 B2 | 12/2004 | Gilboa et al. |
| 6,840,923 B1 | 1/2005 | Lapcevic |
| 6,840,936 B2 | 1/2005 | Sliwa, Jr. et al. |
| 6,849,073 B2 | 2/2005 | Hoey et al. |
| 6,858,005 B2 | 2/2005 | Ohline et al. |
| 6,858,026 B2 | 2/2005 | Sliwa, Jr. et al. |
| 6,863,668 B2 | 3/2005 | Gillespie et al. |
| 6,866,651 B2 | 3/2005 | Constantz |
| 6,887,237 B2 | 5/2005 | McGaffigan |
| 6,892,091 B1 | 5/2005 | Ben-Haim et al. |
| 6,896,690 B1 | 5/2005 | Lambrecht et al. |
| 6,899,672 B2 | 5/2005 | Chin et al. |
| 6,915,154 B1 | 7/2005 | Docherty et al. |
| 6,916,284 B2 | 7/2005 | Moriyama |
| 6,923,805 B1 | 8/2005 | LaFontaine et al. |
| 6,929,010 B2 | 8/2005 | Vaska et al. |
| 6,932,809 B2 | 8/2005 | Sinofsky |
| 6,939,348 B2 | 9/2005 | Malecki et al. |
| 6,942,657 B2 | 9/2005 | Sinofsky et al. |
| 6,949,095 B2 | 9/2005 | Vaska et al. |
| 6,953,457 B2 | 10/2005 | Farr et al. |
| 6,955,173 B2 | 10/2005 | Lesh |
| 6,962,589 B2 | 11/2005 | Mulier et al. |
| 6,971,394 B2 | 12/2005 | Sliwa, Jr. et al. |
| 6,974,464 B2 | 12/2005 | Quijano et al. |
| 6,979,290 B2 | 12/2005 | Mourlas et al. |
| 6,982,740 B2 | 1/2006 | Adair et al. |
| 6,984,232 B2 | 1/2006 | Vanney et al. |
| 6,994,094 B2 | 2/2006 | Schwartz |
| 7,019,610 B2 | 3/2006 | Creighton, IV et al. |
| 7,025,746 B2 | 4/2006 | Tal |
| 7,030,904 B2 | 4/2006 | Adair et al. |
| 7,041,098 B2 | 5/2006 | Farley et al. |
| 7,042,487 B2 | 5/2006 | Nakashima |
| 7,044,135 B2 | 5/2006 | Lesh |
| 7,052,493 B2 | 5/2006 | Vaska et al. |
| 7,090,683 B2 | 8/2006 | Brock et al. |
| 7,118,566 B2 | 10/2006 | Jahns |
| 7,156,845 B2 | 1/2007 | Mulier et al. |
| 7,163,534 B2 | 1/2007 | Brucker et al. |
| 7,166,537 B2 | 1/2007 | Jacobsen et al. |
| 7,169,144 B2 | 1/2007 | Hoey et al. |
| 7,186,214 B2 | 3/2007 | Ness |
| 7,207,984 B2 | 4/2007 | Farr et al. |
| 7,217,268 B2 | 5/2007 | Eggers et al. |
| 7,242,832 B2 | 7/2007 | Carlin et al. |
| 7,247,155 B2 | 7/2007 | Hoey et al. |
| 7,261,711 B2 | 8/2007 | Mulier et al. |
| 7,263,397 B2 | 8/2007 | Hauck et al. |
| 7,276,061 B2 | 10/2007 | Schaer et al. |
| 7,309,328 B2 | 12/2007 | Kaplan et al. |
| 7,416,552 B2 | 8/2008 | Paul et al. |

(56) References Cited

U.S. PATENT DOCUMENTS

| | | | |
|---|---|---|---|
| 7,435,248 B2 | 10/2008 | Taimisto et al. | |
| 7,527,625 B2 | 5/2009 | Knight et al. | |
| 7,534,204 B2 | 5/2009 | Starksen et al. | |
| 7,569,052 B2 | 8/2009 | Phan et al. | |
| 7,736,347 B2 | 6/2010 | Kaplan et al. | |
| 7,758,499 B2 | 7/2010 | Adler | |
| 7,860,555 B2 | 12/2010 | Saadat | |
| 7,860,556 B2 | 12/2010 | Saadat | |
| 7,901,348 B2* | 3/2011 | Soper et al. | 600/117 |
| 8,050,746 B2 | 11/2011 | Saadat et al. | |
| 8,078,266 B2 | 12/2011 | Saadat et al. | |
| 8,131,350 B2 | 3/2012 | Saadat et al. | |
| 8,137,333 B2 | 3/2012 | Saadat et al. | |
| 8,187,189 B2* | 5/2012 | Jung et al. | 600/443 |
| 8,333,012 B2 | 12/2012 | Rothe et al. | |
| 8,382,662 B2* | 2/2013 | Soper et al. | 600/182 |
| 2001/0005789 A1 | 6/2001 | Root et al. | |
| 2001/0020126 A1 | 9/2001 | Swanson et al. | |
| 2001/0031912 A1 | 10/2001 | Adler | |
| 2001/0039416 A1 | 11/2001 | Moorman et al. | |
| 2001/0047136 A1 | 11/2001 | Domanik et al. | |
| 2001/0047184 A1 | 11/2001 | Connors | |
| 2001/0052930 A1 | 12/2001 | Adair et al. | |
| 2002/0004644 A1 | 1/2002 | Koblish | |
| 2002/0026145 A1 | 2/2002 | Bagaoisan et al. | |
| 2002/0054852 A1 | 5/2002 | Cate | |
| 2002/0065455 A1 | 5/2002 | Ben-Haim et al. | |
| 2002/0068853 A1 | 6/2002 | Adler et al. | |
| 2002/0080248 A1 | 6/2002 | Adair et al. | |
| 2002/0087166 A1 | 7/2002 | Brock et al. | |
| 2002/0087169 A1 | 7/2002 | Brock et al. | |
| 2002/0091304 A1 | 7/2002 | Ogura et al. | |
| 2002/0138088 A1 | 9/2002 | Nash et al. | |
| 2002/0165598 A1 | 11/2002 | Wahr et al. | |
| 2002/0169377 A1 | 11/2002 | Khairkhahan et al. | |
| 2003/0009085 A1 | 1/2003 | Arai et al. | |
| 2003/0035156 A1 | 2/2003 | Cooper | |
| 2003/0036698 A1 | 2/2003 | Kohler et al. | |
| 2003/0069593 A1 | 4/2003 | Tremulis et al. | |
| 2003/0120142 A1 | 6/2003 | Dubuc et al. | |
| 2003/0130572 A1 | 7/2003 | Phan et al. | |
| 2003/0144657 A1 | 7/2003 | Bowe et al. | |
| 2003/0171741 A1 | 9/2003 | Ziebol et al. | |
| 2003/0181939 A1 | 9/2003 | Bonutti | |
| 2003/0208222 A1 | 11/2003 | Zadno-Azizi | |
| 2003/0212394 A1 | 11/2003 | Pearson et al. | |
| 2003/0216720 A1 | 11/2003 | Sinofsky et al. | |
| 2003/0220574 A1 | 11/2003 | Markus et al. | |
| 2003/0222325 A1 | 12/2003 | Jacobsen et al. | |
| 2004/0006333 A1 | 1/2004 | Arnold et al. | |
| 2004/0049211 A1 | 3/2004 | Tremulis et al. | |
| 2004/0054335 A1 | 3/2004 | Lesh et al. | |
| 2004/0054389 A1 | 3/2004 | Osypka | |
| 2004/0082833 A1 | 4/2004 | Adler | |
| 2004/0097788 A1 | 5/2004 | Mourlas et al. | |
| 2004/0117032 A1 | 6/2004 | Roth | |
| 2004/0133113 A1 | 7/2004 | Krishnan | |
| 2004/0138707 A1 | 7/2004 | Greenhalgh | |
| 2004/0147806 A1 | 7/2004 | Adler | |
| 2004/0147911 A1 | 7/2004 | Sinofsky | |
| 2004/0147912 A1 | 7/2004 | Sinofsky | |
| 2004/0147913 A1 | 7/2004 | Sinofsky | |
| 2004/0158143 A1 | 8/2004 | Flaherty et al. | |
| 2004/0158289 A1 | 8/2004 | Girouard et al. | |
| 2004/0167503 A1 | 8/2004 | Sinofsky | |
| 2004/0181237 A1 | 9/2004 | Forde et al. | |
| 2004/0199052 A1 | 10/2004 | Banik et al. | |
| 2004/0210239 A1 | 10/2004 | Nash et al. | |
| 2004/0215180 A1 | 10/2004 | Starkebaum et al. | |
| 2004/0215183 A1 | 10/2004 | Hoey et al. | |
| 2004/0220471 A1 | 11/2004 | Schwartz | |
| 2004/0230131 A1 | 11/2004 | Kassab et al. | |
| 2004/0248837 A1 | 12/2004 | Raz et al. | |
| 2004/0249367 A1 | 12/2004 | Saadat et al. | |
| 2004/0254523 A1 | 12/2004 | Fitzgerald et al. | |
| 2004/0260182 A1 | 12/2004 | Zuluaga et al. | |
| 2005/0014995 A1* | 1/2005 | Amundson et al. | 600/105 |
| 2005/0015048 A1 | 1/2005 | Chiu et al. | |
| 2005/0020914 A1 | 1/2005 | Amundson et al. | |
| 2005/0027163 A1 | 2/2005 | Chin et al. | |
| 2005/0038419 A9 | 2/2005 | Arnold et al. | |
| 2005/0059862 A1 | 3/2005 | Phan | |
| 2005/0059954 A1 | 3/2005 | Constantz | |
| 2005/0059965 A1 | 3/2005 | Eberl et al. | |
| 2005/0065504 A1 | 3/2005 | Melsky et al. | |
| 2005/0090818 A1 | 4/2005 | Pike, Jr. et al. | |
| 2005/0096643 A1 | 5/2005 | Brucker et al. | |
| 2005/0101984 A1 | 5/2005 | Chanduszko et al. | |
| 2005/0107736 A1 | 5/2005 | Landman et al. | |
| 2005/0119523 A1 | 6/2005 | Starksen et al. | |
| 2005/0124969 A1 | 6/2005 | Fitzgerald et al. | |
| 2005/0131401 A1 | 6/2005 | Malecki et al. | |
| 2005/0154252 A1 | 7/2005 | Sharkey et al. | |
| 2005/0158899 A1 | 7/2005 | Jacobsen et al. | |
| 2005/0159702 A1 | 7/2005 | Sekiguchi et al. | |
| 2005/0165279 A1 | 7/2005 | Adler et al. | |
| 2005/0165391 A1 | 7/2005 | Maguire et al. | |
| 2005/0165466 A1 | 7/2005 | Morris et al. | |
| 2005/0182295 A1* | 8/2005 | Soper et al. | 600/117 |
| 2005/0182465 A1 | 8/2005 | Ness | |
| 2005/0197530 A1 | 9/2005 | Wallace et al. | |
| 2005/0197623 A1 | 9/2005 | Leeflang et al. | |
| 2005/0215895 A1 | 9/2005 | Popp et al. | |
| 2005/0222557 A1 | 10/2005 | Baxter et al. | |
| 2005/0222558 A1 | 10/2005 | Baxter et al. | |
| 2005/0228452 A1 | 10/2005 | Mourlas et al. | |
| 2005/0234436 A1 | 10/2005 | Baxter et al. | |
| 2005/0234437 A1 | 10/2005 | Baxter et al. | |
| 2005/0267328 A1 | 12/2005 | Blumzvig et al. | |
| 2005/0267452 A1 | 12/2005 | Farr et al. | |
| 2006/0009715 A1 | 1/2006 | Khairkhahan et al. | |
| 2006/0009737 A1 | 1/2006 | Whiting et al. | |
| 2006/0015096 A1 | 1/2006 | Hauck et al. | |
| 2006/0022234 A1 | 2/2006 | Adair et al. | |
| 2006/0025651 A1 | 2/2006 | Adler et al. | |
| 2006/0025787 A1 | 2/2006 | Morales et al. | |
| 2006/0030844 A1 | 2/2006 | Knight et al. | |
| 2006/0069303 A1 | 3/2006 | Couvillon et al. | |
| 2006/0074398 A1 | 4/2006 | Whiting et al. | |
| 2006/0084839 A1 | 4/2006 | Mourlas et al. | |
| 2006/0084945 A1 | 4/2006 | Moll et al. | |
| 2006/0089637 A1 | 4/2006 | Werneth et al. | |
| 2006/0111614 A1 | 5/2006 | Saadat et al. | |
| 2006/0122587 A1 | 6/2006 | Sharareh | |
| 2006/0146172 A1 | 7/2006 | Jacobsen et al. | |
| 2006/0149134 A1* | 7/2006 | Soper et al. | 600/182 |
| 2006/0149331 A1 | 7/2006 | Mann et al. | |
| 2006/0155242 A1 | 7/2006 | Constantz | |
| 2006/0161133 A1 | 7/2006 | Laird et al. | |
| 2006/0167439 A1 | 7/2006 | Kalser et al. | |
| 2006/0183992 A1 | 8/2006 | Kawashima | |
| 2006/0184048 A1 | 8/2006 | Saadat | |
| 2006/0217755 A1 | 9/2006 | Eversull et al. | |
| 2006/0224167 A1 | 10/2006 | Weisenburgh et al. | |
| 2006/0253113 A1 | 11/2006 | Arnold et al. | |
| 2006/0258909 A1 | 11/2006 | Saadat et al. | |
| 2006/0271032 A1 | 11/2006 | Chin et al. | |
| 2007/0005019 A1 | 1/2007 | Okishige | |
| 2007/0015964 A1 | 1/2007 | Eversull et al. | |
| 2007/0016130 A1 | 1/2007 | Leeflang et al. | |
| 2007/0043338 A1 | 2/2007 | Moll et al. | |
| 2007/0043413 A1 | 2/2007 | Eversull et al. | |
| 2007/0049923 A1 | 3/2007 | Jahns | |
| 2007/0055142 A1 | 3/2007 | Webler | |
| 2007/0078451 A1 | 4/2007 | Arnold et al. | |
| 2007/0083187 A1 | 4/2007 | Eversull et al. | |
| 2007/0083217 A1 | 4/2007 | Eversull et al. | |
| 2007/0093808 A1 | 4/2007 | Mulier et al. | |
| 2007/0100241 A1 | 5/2007 | Adler | |
| 2007/0100324 A1 | 5/2007 | Tempel et al. | |
| 2007/0106146 A1 | 5/2007 | Altmann et al. | |
| 2007/0106214 A1 | 5/2007 | Gray et al. | |
| 2007/0106287 A1 | 5/2007 | O'Sullivan | |
| 2007/0135826 A1 | 6/2007 | Zaver et al. | |

(56) References Cited

U.S. PATENT DOCUMENTS

| | | | |
|---|---|---|---|
| 2007/0167801 A1 | 7/2007 | Webler et al. | |
| 2007/0167828 A1 | 7/2007 | Saadat | |
| 2007/0255097 A1* | 11/2007 | Jung et al. | 600/108 |
| 2007/0265609 A1 | 11/2007 | Thapliyal et al. | |
| 2007/0265610 A1 | 11/2007 | Thapliyal et al. | |
| 2007/0270686 A1 | 11/2007 | Ritter et al. | |
| 2007/0282371 A1 | 12/2007 | Lee et al. | |
| 2007/0287886 A1 | 12/2007 | Saadat | |
| 2007/0293724 A1 | 12/2007 | Saadat et al. | |
| 2008/0009747 A1 | 1/2008 | Saadat et al. | |
| 2008/0009859 A1 | 1/2008 | Auth et al. | |
| 2008/0015445 A1 | 1/2008 | Saadat et al. | |
| 2008/0015563 A1 | 1/2008 | Hoey et al. | |
| 2008/0015569 A1 | 1/2008 | Saadat et al. | |
| 2008/0027464 A1 | 1/2008 | Moll et al. | |
| 2008/0033241 A1 | 2/2008 | Peh et al. | |
| 2008/0033290 A1 | 2/2008 | Saadat et al. | |
| 2008/0045827 A1* | 2/2008 | Rongen et al. | 600/407 |
| 2008/0057106 A1 | 3/2008 | Erickson et al. | |
| 2008/0058590 A1 | 3/2008 | Saadat et al. | |
| 2008/0058591 A1 | 3/2008 | Saadat et al. | |
| 2008/0058650 A1 | 3/2008 | Saadat et al. | |
| 2008/0058836 A1 | 3/2008 | Moll et al. | |
| 2008/0097476 A1 | 4/2008 | Peh et al. | |
| 2008/0183081 A1 | 7/2008 | Lys et al. | |
| 2008/0188759 A1 | 8/2008 | Saadat et al. | |
| 2008/0214889 A1 | 9/2008 | Saadat et al. | |
| 2008/0228032 A1 | 9/2008 | Starksen et al. | |
| 2008/0275300 A1 | 11/2008 | Rothe et al. | |
| 2008/0281293 A1 | 11/2008 | Peh et al. | |
| 2008/0287790 A1 | 11/2008 | Li | |
| 2008/0287805 A1 | 11/2008 | Li | |
| 2009/0030276 A1 | 1/2009 | Saadat et al. | |
| 2009/0030412 A1 | 1/2009 | Willis et al. | |
| 2009/0054803 A1 | 2/2009 | Saadat et al. | |
| 2009/0062790 A1 | 3/2009 | Malchano et al. | |
| 2009/0076489 A1 | 3/2009 | Welches et al. | |
| 2009/0076498 A1 | 3/2009 | Saadat et al. | |
| 2009/0082623 A1 | 3/2009 | Rothe et al. | |
| 2009/0125022 A1 | 5/2009 | Saadat et al. | |
| 2009/0143640 A1 | 6/2009 | Saadat et al. | |
| 2009/0187074 A1 | 7/2009 | Saadat et al. | |
| 2009/0203962 A1 | 8/2009 | Miller et al. | |
| 2009/0221871 A1* | 9/2009 | Peh et al. | 600/118 |
| 2009/0227999 A1 | 9/2009 | Willis et al. | |
| 2009/0264727 A1 | 10/2009 | Markowitz et al. | |
| 2009/0267773 A1 | 10/2009 | Markowitz et al. | |
| 2009/0275799 A1 | 11/2009 | Saadat et al. | |
| 2009/0275842 A1 | 11/2009 | Saadat et al. | |
| 2009/0299363 A1 | 12/2009 | Saadat et al. | |
| 2009/0326572 A1 | 12/2009 | Peh et al. | |
| 2010/0004506 A1 | 1/2010 | Saadat | |
| 2010/0004633 A1 | 1/2010 | Rothe et al. | |
| 2010/0004661 A1 | 1/2010 | Verin et al. | |
| 2010/0010311 A1 | 1/2010 | Miller et al. | |
| 2010/0016662 A1* | 1/2010 | Salsman et al. | 600/109 |
| 2010/0094081 A1 | 4/2010 | Rothe et al. | |
| 2010/0130836 A1 | 5/2010 | Malchano et al. | |
| 2010/0198081 A1* | 8/2010 | Hanlin et al. | 600/478 |
| 2010/0292558 A1* | 11/2010 | Saadat et al. | 600/407 |
| 2011/0060227 A1 | 3/2011 | Saadat | |
| 2011/0060298 A1 | 3/2011 | Saadat | |
| 2011/0144576 A1 | 6/2011 | Rothe et al. | |
| 2011/0301418 A1* | 12/2011 | Gharib et al. | 600/181 |
| 2011/0306833 A1 | 12/2011 | Saadat et al. | |
| 2012/0004544 A9 | 1/2012 | Saadat et al. | |
| 2012/0004577 A1 | 1/2012 | Saadat et al. | |
| 2012/0059366 A1 | 3/2012 | Drews et al. | |
| 2012/0277596 A1* | 11/2012 | Jung et al. | 600/479 |

FOREIGN PATENT DOCUMENTS

| | | |
|---|---|---|
| EP | 0301288 A1 | 2/1999 |
| JP | 59093413 A | 5/1984 |
| JP | 59-181315 | 10/1984 |
| JP | 01-221133 | 9/1989 |
| JP | 03-284265 | 12/1991 |
| JP | 05-103746 | 4/1993 |
| JP | 09-051897 | 2/1997 |
| JP | 11-299725 | 11/1999 |
| JP | 2001-258822 | 9/2001 |
| WO | WO 92/21292 | 12/1992 |
| WO | WO 94/07413 | 4/1994 |
| WO | WO 95/03843 | 2/1995 |
| WO | WO 98/18388 | 5/1998 |
| WO | WO 03/039350 | 5/2003 |
| WO | WO 03/053491 | 7/2003 |
| WO | WO 03/101287 | 12/2003 |
| WO | WO 2004/043272 | 5/2004 |
| WO | WO 2004/080508 | 9/2004 |
| WO | WO 2005/070330 | 8/2005 |
| WO | WO 2005/077435 | 8/2005 |
| WO | WO 2005/081202 | 9/2005 |
| WO | WO 2006/017517 | 2/2006 |
| WO | WO 2006/024015 | 3/2006 |
| WO | WO 2006/083794 | 8/2006 |
| WO | WO 2006/091597 | 8/2006 |
| WO | WO 2006/126979 | 11/2006 |
| WO | WO 2007/067323 | 6/2007 |
| WO | WO 2007/079268 | 7/2007 |
| WO | WO 2007/133845 | 11/2007 |
| WO | WO 2007/134258 | 11/2007 |
| WO | WO 2008/015625 | 2/2008 |
| WO | WO 2008/021994 | 2/2008 |
| WO | WO 2008/021997 | 2/2008 |
| WO | WO 2008/021998 | 2/2008 |
| WO | WO 2008/024261 | 2/2008 |
| WO | WO 2008/079828 | 7/2008 |
| WO | WO 2009/112262 | 9/2009 |

OTHER PUBLICATIONS

Avitall, "Right-Sided Driven Atrial Fibrillation in a Sterile Pericarditis Dog Model", *PACE*, vol. 17, p. 774, 1994.

Avitall, "Vagally Mediated Atrial Fibrillation in a Dog Model can be Ablated by Placing Linear Radiofrequency Lesions at the Junction of the Right Atrial Appendage and the Superior Vena Cava", *PACE*, vol. 18, p. 857, 1995.

Baker, "Nonpharmacologic Approaches to the Treatment of Atrial Fibrillation and Atrial Flutter", *J. Cardiovasc. Electrophysiol.*, vol. 6, pp. 972-978, 1995.

Bhakta, "Principles of Electroanatomic Mapping", *Indian Pacing & Electrophysiol J.*, vol. 8, No. 1, pp. 32-50, 2008.

Bidoggia, "Transseptal Left Heart Catheterization: Usefulness of the Intracavitary Electrocardiogram in the Localization of the Fossa Ovalis", *Cathet Cardiovasc Diagn.*, vol. 24, No. 3, pp. 221-225, 1991.

Bredikis, "Surgery of Tachyarrhythmia: Intracardiac Closed Heart Cryoablation", *PACE*, vol. 13, pp. 1980-1984, 1990.

Cox, "Cardiac Surgery for Arrhythmias", *J. Cardiovasc. Electrophysiol.*, vol. 15, pp. 250-262, 2004.

Cox, "Five-Year Experience With the Maze Procedure for Atrial Fibrillation", The *Annals Thoracic Surgery*, vol. 56, pp. 814-824, 1993.

Cox, "Modification of the Maze Procedure for Atrial Flutter and Atrial Fibrillation", *The Journal of Thoracic and Cardiovascular Surgery*, vol. 110, pp. 473-484, 1995.

Cox, "The Status of Surgery for Cardiac Arrhythmias", *Circulation*, vol. 71, pp. 413-417, 1985.

Cox, "The Surgical Treatment of Atrial Fibrillation", *The Journal of Thoracic and Cardiovascular Surgery*, vol. 101, pp. 584-592, 1991.

Elvan, Replication of the "Maze" Procedure by Radiofrequency Catheter Ablation Reduces the Ability to Induce Atrial Fibrillation, PACE, vol. 17, p. 774, 1994.

Elvan, Radiofrequency Catheter Ablation (RFCA) of the Atria Effectively Abolishes Pacing Induced Chronic Atrial Fibrillation, PACE, vol. 18, p. 856, 1995.

Elvan, Radiofrequency Catheter Ablation of the Atria Reduces Inducibility and Duration of Atrial Fibrillation in Dogs, *Circulation*, vol. 91, pp. 2235-2244, 1995.

(56) References Cited

OTHER PUBLICATIONS

European Patent Application No. 06734083.6 filed Jan. 30, 2006 in the name of Saadat et al., Examination Communication mailed May 18, 2010.
European Patent Application No. 06734083.6 filed Jan. 30, 2006 in the name of Saadat et al., extended European Search Report mailed Jul. 1, 2009.
European Patent Application No. 06734083.6 filed Jan. 30, 2006 in the name of Saadat et al., office action mailed Oct. 23, 2009.
European Patent Application No. 07841754.0 filed Aug. 31, 2007 in the name of Saadat et al., Supplemental European Search Report mailed Jun. 30, 2010.
European Patent Application No. 08746822.9 filed Apr. 24, 2008 in the name of Rothe et al., European Search Report mailed Mar. 29, 2010.
European Patent Application No. 08746822.9 filed Apr. 24, 2008 in the name of Rothe et al., Office Action mailed Jul. 13, 2010.
Fieguth, Inhibition of Atrial Fibrillation by Pulmonary Vein Isolation and Auricular Resection—Experimental Study in a Sheep Model, European J. Cardiothorac. Surg., vol. 11, pp. 714-721, 1997.
Hoey, Intramural Ablation Using Radiofrequency Energy via Screw-Tip Catheter and Saline Electrode, PACE, vol. 18, p. 487, 1995.
Huang, Increase in the Lesion Size and Decrease in the Impedance Rise with a Saline Infusion Electrode Catheter for Radiofrequency, Circulation, vol. 80, No. 4, pp. II-324, 1989.
Moser, Angioscopic Visualization of Pulmonary Emboli, CHEST, vol. 77, No. 2, pp. 198-201, 1980.
Nakamura, Percutaneous Intracardiac Surgery With Cardioscopic Guidance, SPIE, vol. 1652, pp. 214-216, 1992.
Pappone, Circumferential Radiofrequency Ablation of Pulmonary Vein Ostia, Circulation, vol. 102, pp. 2619-2628, 2000.
Sethi, Transseptal Catheterization for the Electrophysiologist: Modification with a "View", J. Interv. Card. Electrophysiol., vol. 5, pp. 97-99, 2001, Kluwer Academic Publishers, Netherlands.
Thiagalingam, Cooled Needle Catheter Ablation Creates Deeper and Wider Lesions than Irrigated Tip Catheter Ablation, J. Cardiovasc. Electrophysiol., vol. 16, pp. 1-8, 2005.
U.S. Appl. No. 11/259,498, filed Oct. 25, 2005 in the name of Saadat et al., Non-final Office Action mailed Feb. 25, 2010.
U.S. Appl. No. 11/560,742, filed Nov. 16, 2006 in the name of Saadat, Non-final Office Action mailed Jun. 10, 2010.
U.S. Appl. No. 11/687,597, filed Mar. 16, 2007 in the name of Saadat et al., Non-final Office Action mailed Jul. 21, 2010.
U.S. Appl. No. 11/828,267, filed Jul. 25, 2007 in the name of Saadat et al., Non-final Office Action mailed Jan. 14, 2010.
U.S. Appl. No. 12/117,655, filed May 8, 2008 in the name of Peh et al., Final Office Action mailed Mar. 1, 2010.
U.S. Appl. No. 12/117,655, filed May 8, 2008 in the name of Saadat et al., Non-final Office Action mailed Jun. 8, 2009.
U.S. Appl. No. 61/286,283, filed Dec. 14, 2009 in the name of Rothe et al.
U.S. Appl. No. 61/297,462, filed Jan. 22, 2010 in the name of Rothe et al.
Uchida, Developmental History of Cardioscopes, Coronary Angioscopy, pp. 187-197, 2001, Futura Publishing Co., Armonk, NY.
Willkampf, Radiofrequency Ablation with a Cooled Porous Electrode Catheter, JACC, vol. 11, No. 2, p. 17A, 1988.
U.S. Appl. No. 11/775,771, filed Jul. 10, 2007 in the name of Saadat et al., Non-final Office Action mailed Aug. 27, 2010.
U.S. Appl. No. 11/828,267, filed Jul. 25, 2007 in the name of Saadat et al., final Office Action mailed Sep. 16, 2010.
U.S. Appl. No. 11/259,498, filed Oct. 25, 2005 in the name of Saadat, Notice of Allowance mailed Nov. 15, 2010.
U.S. Appl. No. 11/560,742, filed Nov. 16, 2006 in the name of Saadat, Notice of Allowance mailed Nov. 15, 2010.
U.S. Appl. No. 12/464,800, filed May 12, 2009 in the name of Peh et al., non-final Office Action mailed Nov. 24, 2010.
U.S. Appl. No. 11/848,429, filed Aug. 31, 2007 in the name of Peh et al., non-final Office Action mailed Nov. 24, 2010.
European Patent Application No. 06734083.6 filed Jan. 30, 2006 in the name of Voyage Medical, Inc., Office Action mailed Nov. 12, 2010.
European Patent Application No. 07812146.4 filed Jun. 14, 2007 in the name of Voyage Medical, Inc., European Search Report mailed Nov. 18, 2010.
European Patent Application No. 07799466.3 filed Jul. 10, 2007 in the name of Voyage Medical, Inc., European Search Report mailed Nov. 18, 2010.
U.S. Appl. No. 12/117,655, filed May 8, 2008 in the name of Peh et al., non-final Office Action mailed Dec. 16, 2010.
U.S. Appl. No. 12/026,455, filed Feb. 5, 2008 in the name of Saadat et al., non-final Office Action mailed Dec. 27, 2010.
U.S. Appl. No. 12/947,198, filed Nov. 16, 2010 in the name of Saadat, non-final Office Action mailed Feb. 18, 2011.
U.S. Appl. No. 11/560,732, filed Nov. 16, 2006 in the name of Saadat, Notice of Allowance mailed Feb. 3, 2011.
U.S. Appl. No. 12/947,246, filed Nov. 16, 2006 in the name of Saadat, Notice of Allowance mailed Feb. 18, 2011.
U.S. Appl. No. 11/687,597, filed Mar. 16, 2007 in the name of Saadat, Notice of Allowance mailed Feb. 24, 2011.
U.S. Appl. No. 11/560,732, filed Mar. 16, 2007 in the name of Saadat, Notice of Allowance mailed Feb. 24, 2011.
U.S. Appl. No. 11/848,207, filed Aug. 30, 2007 in the name of Saadat et al., non-final Office Action mailed Feb. 25, 2011.
Japanese Patent Application No. 2007-554156 filed Jan. 30, 2006 in the name of Voyage Medical, Inc., Office Action mailed Feb. 15, 2011.
European Patent Application No. 07758716.0 filed Mar. 16, 2007 in the name of Voyage Medical, Inc., Supplemental European Search Report mailed Feb. 28, 2011.
U.S. Appl. No. 11/848,202, filed Aug. 30, 2007 in the name of Saadat et al., non-final Office Action mailed Mar. 11, 2011.
U.S. Appl. No. 11/763,399, filed Jun. 14, 2007 in the name of Saadat et al., non-final Office Action mailed Apr. 11, 2011.
U.S. Appl. No. 12/499,011, filed Jul. 7, 2009 in the name of Rothe et al., non-final Office Action mailed Apr. 12, 2011.
U.S. Appl. No. 12/367,019, filed Feb. 6, 2009 in the name of Miller et al., non-final Office Action mailed Apr. 22, 2011.
U.S. Appl. No. 11/959,158, filed Dec. 18, 2007 in the name of Saadat et al., non-final Office Action mailed Apr. 25, 2011.
U.S. Appl. No. 11/848,532, filed Aug. 31, 2007 in the name of Saadat et al., non-final Office Action mailed Apr. 26, 2011.
U.S. Appl. No. 11/828,281, filed Jul. 25, 2007 in the name of Peh et al., non-final Office Action mailed Apr. 27, 2011.
U.S. Appl. No. 11/961,950, filed Dec. 20, 2007 in the name of Saadat et al., non-final Office Action mailed May 9, 2011.
U.S. Appl. No. 11/961,995, filed Dec. 20, 2007 in the name of Saadat et al., non-final Office Action mailed May 9, 2011.
U.S. Appl. No. 11/962,029, filed Dec. 20, 2007 in the name of Saadat et al., non-final Office Action mailed May 9, 2011.
U.S. Appl. No. 11/828,267, filed Jul. 25, 2007 in the name of Saadat et al., non-final Office Action mailed May 11, 2011.
Japanese Patent Application No. 2009-500630 filed Mar. 16, 2007 in the name of Voyage Medical, Inc., Office Action mailed Apr. 27, 2011.
U.S. Appl. No. 11/775,771, filed Jul. 10, 2007 in the name of Saadat et al., final Office Action mailed May 12, 2011.
U.S. Appl. No. 11/877,386, filed Oct. 23, 2007 in the name of Saadat et al., non-final Office Action mailed May 20, 2011.
U.S. Appl. No. 11/775,819, filed Jul. 10, 2007 in the name of Saadat et al., non-final Office Action mailed May 20, 2011.
U.S. Appl. No. 11/775,837, filed Jul. 10, 2007 in the name of Saadat et al., non-final Office Action mailed May 23, 2011.
U.S. Appl. No. 12/117,655, filed May 8, 2008 in the name of Peh et al., final Office Action mailed Jun. 2, 2011.
U.S. Appl. No. 12/323,281, filed Nov. 25, 2008 in the name of Saadat et al., non-final Office Action mailed Jun. 7, 2011.
Japanese Patent Application No. 2007-554156 filed Jan. 30, 2006 in the name of Voyage Medical, Inc., Notice of Allowance mailed Jun. 13, 2011.

* cited by examiner

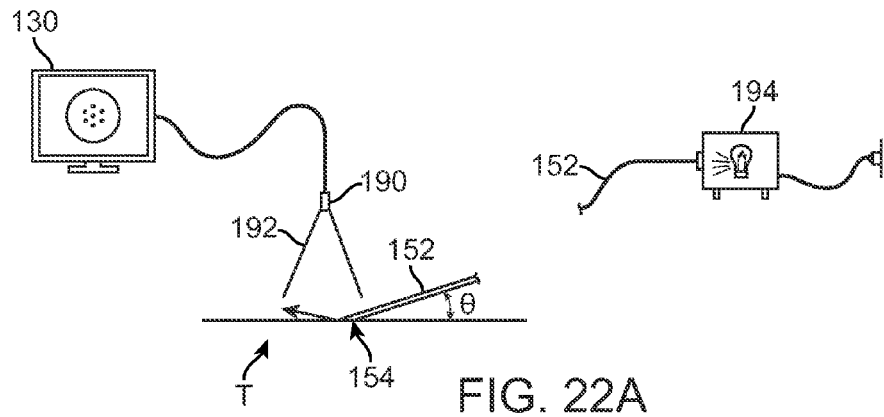
FIG. 22A
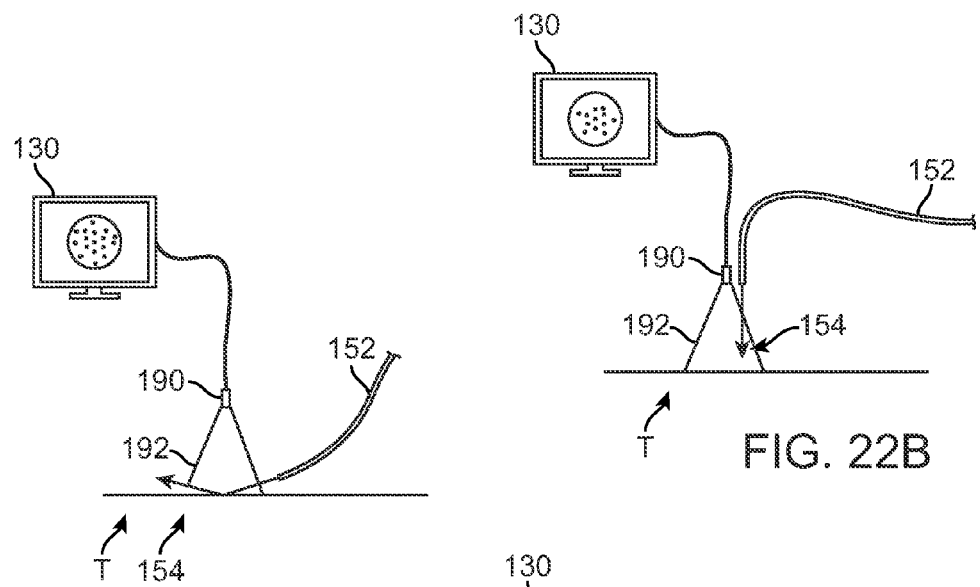
FIG. 22B
FIG. 22C
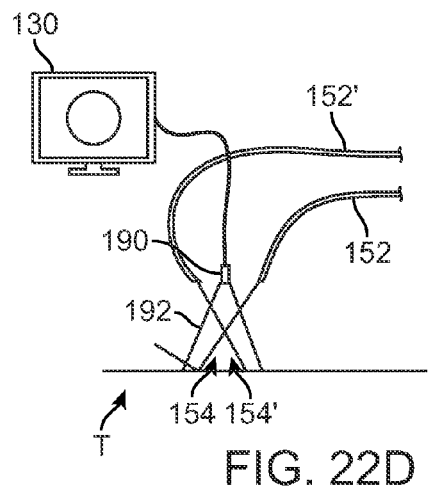
FIG. 22D

IMAGE STABILIZATION TECHNIQUES AND METHODS

CROSS-REFERENCE TO RELATED APPLICATIONS

This application claims the benefit of priority to U.S. Provisional Application 61/304,235 filed Feb. 12, 2010, which is incorporated herein by reference in its entirety.

FIELD OF THE INVENTION

The present invention relates generally to catheter control systems and methods for stabilizing images of moving tissue regions such as a heart which are captured when intravascularly accessing and/or treating regions of the body.

BACKGROUND OF THE INVENTION

Conventional devices for accessing and visualizing interior regions of a body lumen are known. For example, various catheter devices are typically advanced within a patient's body, e.g., intravascularly, and advanced into a desirable position within the body. Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, many of the conventional catheter imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. Nos. 5,895,417; 5,941, 845; and 6,129,724, used on the epicardial surface of the heart may be difficult in assuring a transmural lesion or complete blockage of electrical signals. In addition, current devices may have difficulty dealing with varying thickness of tissue through which a transmural lesion is desired.

Conventional accompanying imaging devices, such as fluoroscopy, are unable to detect perpendicular electrode orientation, catheter movement during the cardiac cycle, and image catheter position throughout lesion formation. The absence of real-time visualization also poses the risk of incorrect placement and ablation of structures such as sinus node tissue which can lead to fatal consequences.

Moreover, because of the tortuous nature of intravascular access, devices or mechanisms at the distal end of a catheter positioned within the patient's body, e.g., within a chamber of the heart, are typically no longer aligned with the handle. Steering or manipulation of the distal end of the catheter via control or articulation mechanisms on the handle is easily disorienting to the user as manipulation of a control on the handle in a first direction may articulate the catheter distal end in an unexpected direction depending upon the resulting catheter configuration leaving the user to adjust accordingly. However, this results in reduced efficiency and longer procedure times as well as increased risks to the patient. Accordingly, there is a need for improved catheter control systems which facilitate the manipulation and articulation of a catheter.

SUMMARY OF THE INVENTION

Accordingly, various methods and techniques may be effected to stabilize the images of the tissue when directly visualizing moving regions of tissue, such as the tissue which moves in a beating heart with an imaging assembly positioned in proximity to or against the tissue. Systems and mechanisms are described that can capture and process video images in order to provide a "stabilized" output image and/or create a larger composite image generated from a series of images for the purposes of simplifying the output image for user interpretation during diagnostic and therapeutic procedures.

Typically, images can be captured/recorded by a video camera at a rate of, e.g., 10-100 fps (frames per second), based on the system hardware and software configurations. Much higher video capture rates are also possible in additional variations. The images can then be captured and processed with customizable and/or configurable DSP (digital signal processing) hardware and software at much higher computational speeds (e.g., 1.5-3 kHz as well as relatively slower or faster rates) in order to provide real-time or near real-time analysis of the image data. Additionally, analog signal processing hardware may also be incorporated. A variety of algorithms, e.g., optical flow, image pattern matching, etc. can be used to identify, track and monitor the movement of whole images or features, elements, patterns, and/or structures within the image(s) in order to generate velocity and/or displacement fields that can be utilized by further algorithmic processing to render a more stabilized image. For the imaging assembly, examples of various algorithms which may be utilized may include, e.g., optical flow estimation to compute an approximation to the motion field from time-varying image intensity. Additionally, methods for evaluating motion estimation may also include, e.g., correlation, block matching, feature tracking, energy-based algorithms, as well as, gradient-based approaches, among others.

In some cases, the image frames may be shifted by simple translation and/or rotation and may not contain a significant degree of distortion or other artifacts to greatly simplify the image processing methods and increase overall speed. Alternatively, the hardware and software system can also create a composite image that is comprised (or a combination) of multiple frames during a motion cycle by employing a variety of image stitching algorithms. A graphical feature, e.g., a circle, square, dotted-lines, etc, can be superimposed or overlaid on the composite image in order to indicate the actual position of the camera (image) based on the information obtained from the image tracking software as the camera/hood undergoes a certain excursion, displacement, etc., relative to the target tissue of the organ structure.

An estimate of motion and pixel shifts may also be utilized. For example, a fibrillating heart can achieve 300 bpm (beats per minute), which equals 5 beats per second. Given a video capture rate of 30 fps (frames per second) there would then be roughly 6 frames captured during each beat. Given a typical displacement of, e.g., 1 cm of the camera/hood relative to the plane of the surface of the target tissue per beat, each image may record a displacement of about 1.6 mm per frame. With a field of view (FOV), e.g., of about 7 mm, then each frame may represent an image shift of about 23%. Given an image sensor size of, e.g., 220 pixels×224 pixels, the number of pixels displaced per frame is, e.g., 50 pixels.

Image processing and analysis algorithms may be extremely sensitive to instabilities in, e.g., image intensity, lighting conditions and to variability/instability in the lighting (or image intensity) over the sequence of image frames, as this can interfere with the analysis and/or interpretation of movement within the image. Therefore, mechanisms and methods of carefully controlling the consistency of the lighting conditions may be utilized for ensuring accurate and robust image analysis. Furthermore, mechanisms and methods for highlighting surface features, structures, textures, and/or roughness may also be utilized. For example, a plurality of peripheral light sources, e.g., from flexible light fiber(s), can create even symmetrical illumination or can be tailored to have one or all illuminating sources active or by activating sources near each other in order to provide focused lighting from one edge or possibly alternate the light sources in order to best represent, depict, characterize, highlight features of the tissue, etc. The light source can be configured such that all light sources are from one origin of a given wavelength or the wavelength can be adjusted for each light element. Also, the light bundles can be used to multiplex the light to other different sources so that a given wavelength can be provided at one or more light sources and can be controlled to provide the best feature detection (illumination) and also to provide the most suitable image for feature detection or pattern matching.

As further described herein, light fibers can be located at the periphery of the hood or they can be configured within the hood member. The incidence angle can be tailored such that the reflected light is controlled to minimize glare and other lighting artifacts that could falsely appear as surface features of interest and therefore possibly interfere with the image tracking system. The lighting requirements that provide optimal visual views of the target tissue for the user may vary from the lighting requirements utilized by the software to effectively track features on the target tissue in an automated manner. The lighting conditions can be changed accordingly for different conditions (e.g., direct viewing by the user or under software control) and can be automatically (e.g., software controlled) or manually configurable. Lighting sources could include, e.g., light emitting diodes, lasers, incandescent lights, etc., with a broad spectrum from near-infrared (>760 nm) through the visible light spectrum.

As the camera actively tracks its position relative to the target tissue, the power delivered by the RF generator during ablation may also be controlled as a function of the position of the hood in order to deliver energy to the tissue at a consistent level. In situations where the excursions of the hood/camera occur with varying velocity, the power level may be increased during periods of rapid movements and/or decreased during periods of slower movements such that the average delivery of energy per region/area (per unit time) is roughly constant to minimize regions of incomplete or excessive ablation thus potentially reducing or eliminating damage to surrounding tissue, structures or organs. Alternatively, the tracking of the target tissue may be utilized such that only particular regions in the moving field receive energy whereas other areas in the field receive none (or relatively less energy) by modulating the output power accordingly by effectively gating the power delivery to a location(s) on the target tissue. This technique could ultimately provide higher specificity and focal delivery of ablative energy despite a moving RF electrode system relative to the target tissue.

Active or dynamic control of the hood using control wires, etc., may also be used in order to match/synchronize the excursion of the device with that of the tissue by utilizing surface sensors and/or optical video image to provide feedback to motion control.

BRIEF DESCRIPTION OF THE DRAWINGS

FIGS. 22A to 22D show various examples of various configurations for angling light incident upon the tissue surface.

DETAILED DESCRIPTION OF THE INVENTION

A tissue-imaging and manipulation apparatus described herein is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures. Although intravascular applications are described, other extravascular approaches or applications may be utilized with the devices and methods herein.

Figure 1A:
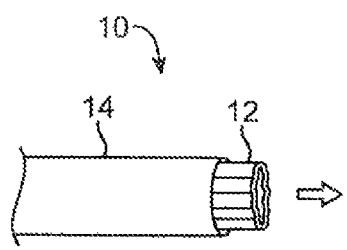
FIG. 1A shows a side view of one variation of a tissue imaging apparatus during deployment from a sheath or delivery catheter.
Figure 1B:
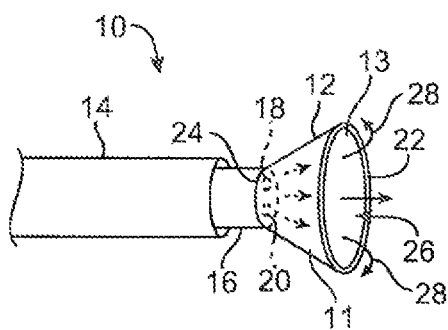
FIG. 1B shows the deployed tissue imaging apparatus of FIG. 1A having an optionally expandable hood or sheath attached to an imaging and/or diagnostic catheter.
Figure 1C:
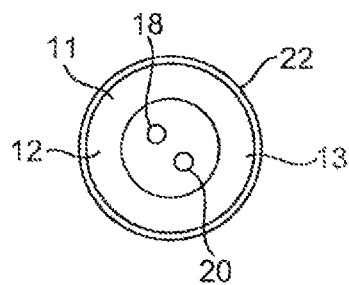
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
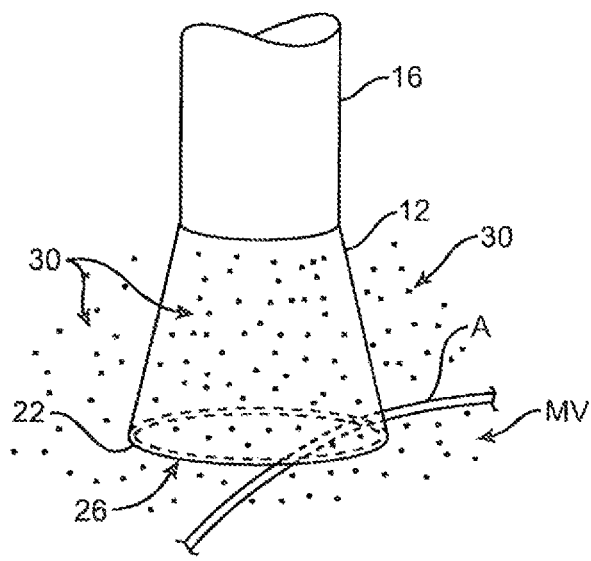
FIGS. 2A and 2B show one example of a deployed tissue imager positioned against or adjacent to the tissue to be imaged and a flow of fluid, such as saline, displacing blood from within the expandable hood.
Figure 2B:
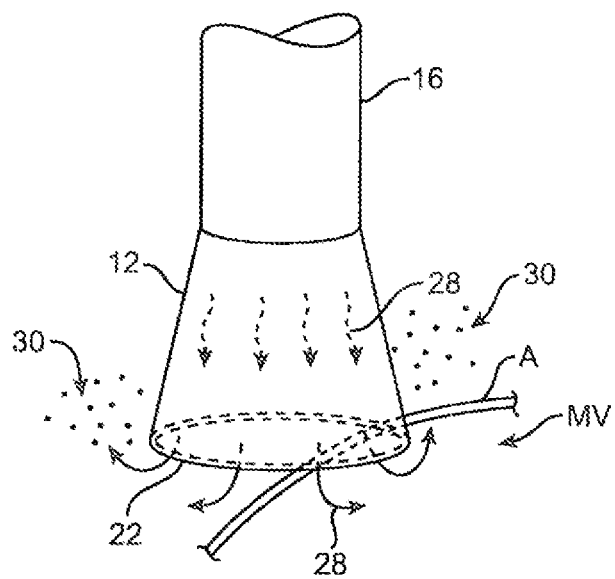

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant back-flow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
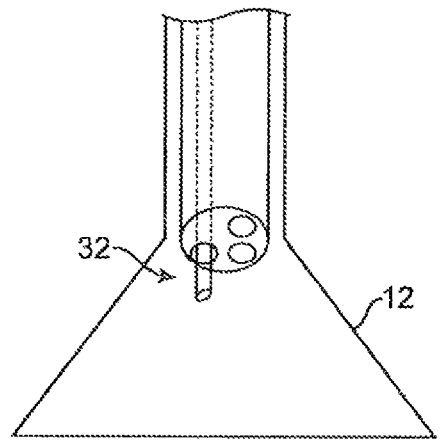
FIGS. 3A and 3B show examples of various visualization imagers which may be utilized within or along the imaging hood.
Figure 3B:
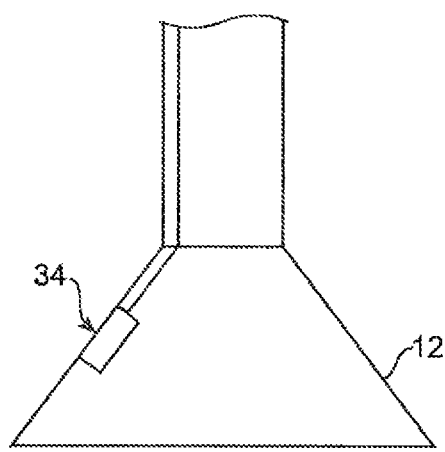

FIG. 3A shows a partial cross-sectional view of an example where one or more optical fiber bundles 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

Figure 4A:
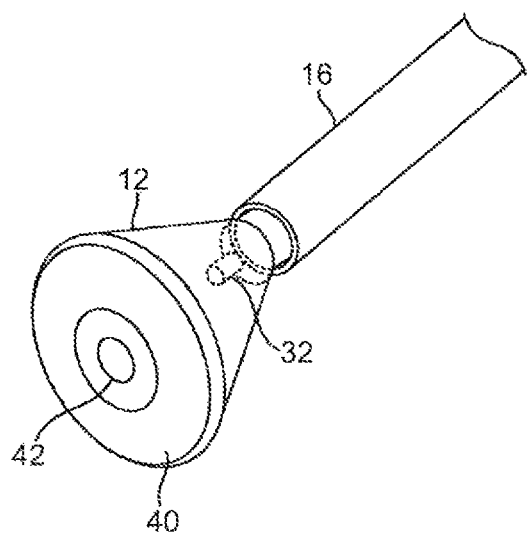
FIGS. 4A and 4B show perspective and end views, respectively, of an imaging hood having at least one layer of a transparent elastomeric membrane over the distal opening of the hood.
Figure 4B:
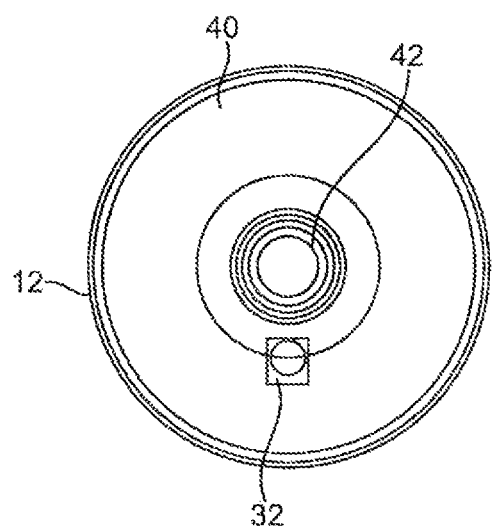

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
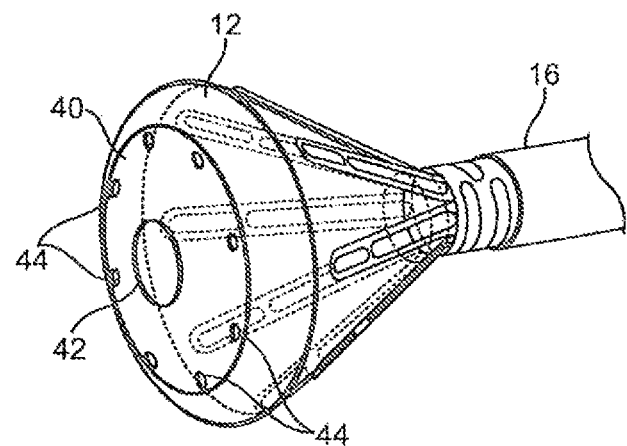
FIGS. 5A and 5B show perspective and end views, respectively, of an imaging hood which includes a membrane with an aperture defined therethrough and a plurality of additional openings defined over the membrane surrounding the aperture.
Figure 5B:
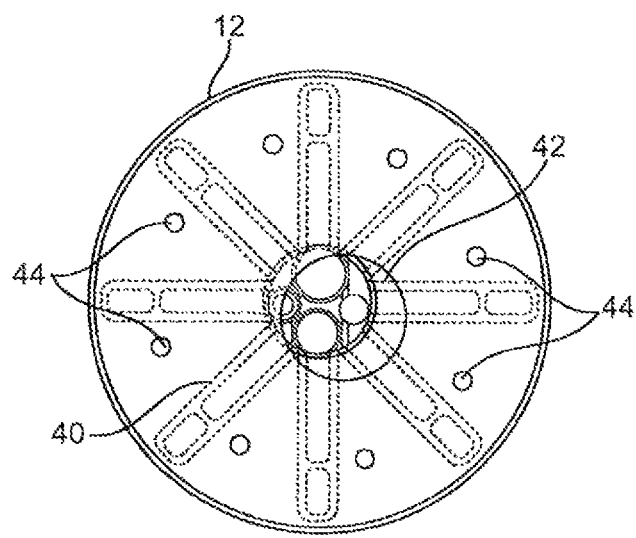

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. patent application Ser. No. 11/259,498 filed Oct. 25, 2005 (U.S. Pat. No. 7,860,555); Ser. No. 11/763,399 filed Jun. 14, 2007 (U.S. Pub. 2007/0293724); and Ser. No. 12/118,439 filed May 9, 2008 (U.S. Pub. 2009/0030412), each of which is incorporated herein by reference in its entirety.

In utilizing the devices and methods above, various procedures may be accomplished. One example of such a procedure is crossing a tissue region such as in a transseptal procedure where a septal wall is pierced and traversed, e.g., crossing from a right atrial chamber to a left atrial chamber in a heart of a subject. Generally, in piercing and traversing a septal wall, the visualization and treatment devices described herein may be utilized for visualizing the tissue region to be pierced as well as monitoring the piercing and access through the tissue. Details of transseptal visualization catheters and methods for transseptal access which may be utilized with the apparatus and methods described herein are described in U.S. patent application Ser. No. 11/763,399 filed Jun. 14, 2007 (U.S. Pat. Pub. 2007/0293724 A1), incorporated herein by reference above. Additionally, details of tissue visualization and manipulation catheter which may be utilized with apparatus and methods described herein are described in U.S. patent application Ser. No. 11/259,498 filed Oct. 25, 2005 (U.S. Pat. Pub. 2006/0184048 A1), also incorporated herein above.

When visualizing moving regions of tissue, such as the tissue which moves in a beating heart, the relative movement between the imaging assembly in the device and the tissue region may result in tissue images which are difficult to capture accurately. Accordingly, various methods and techniques may be effected to stabilize the images of the tissue, e.g., (1) mechanical stabilization of the hood-camera assembly under dynamic control using imaging from the camera or surface sensors or both; (2) software stabilization (algorithmic based stabilization via pattern matching, feature detection, optical flow, etc); (3) sensor-based tracking of excursion of the assembly relative to the tissue (surface optical sensor, accelerometer, EnSite NavX® (St. Jude Medical, Minn.), Carto® Navigation System (Biosense Webster, Calif.), etc.) as feedback into an algorithm; and/or (4) signal feedback of biological functions into an algorithm (EKG, respiration, etc).

Systems and mechanisms are described that can capture and process video images in order to provide a "stabilized" output image and/or create a larger composite image generated from a series of images for the purposes of simplifying the output image for user interpretation during diagnostic and therapeutic procedures.

Typically, images can be captured/recorded by a video camera at a rate of, e.g., 10-100 fps (frames per second), based on the system hardware and software configurations. Much higher video capture rates are also possible in additional variations. The images can then be captured and processed with customizable and/or configurable DSP (digital signal processing) hardware and software at much higher computational speeds (e.g., 1.5-3 kHz as well as relatively slower or faster rates) in order to provide real-time or near real-time analysis of the image data. Additionally, analog signal processing hardware may also be incorporated.

A variety of algorithms, e.g., optical flow, image pattern matching, etc. can be used to identify, track and monitor the movement of whole images or features, elements, patterns, and/or structures within the image(s) in order to generate velocity and/or displacement fields that can be utilized by further algorithmic processing to render a more stabilized image. For example, see B. Horn and B. Schunck. Determining optical flow. *Artificial Intelligence,* 16(1-3):185-203, August 1981. and B. Lucas and T. Kanade. An iterative image registration technique with an application to stereo vision. In *IJCAI*81, pages 674-679, 1981. and J. Shin, S. Kim, S. Kang, S.-W. Lee, J. Paik, B. Abidi, and M. Abidi. Optical flow-based real-time object tracking using non-prior training active feature model. *Real-Time Imaging,* 11(3):204-218, June 2005 and J. Barron, D. Fleet, S. Beauchemin. Performance of Optical Flow Techniques. *International Journal of Computer Vision,* 12 (1):43-77, 1994, D. Fleet, Y. Weiss. Optical Flow Estimation. *Handbook of Mathematical Models in Computer Vision.* (Editors: N. Paragios, et al.). Pages. 239-258, 2005.). Each of these references is incorporated herein by reference in its entirety. For the imaging assembly, examples of various algorithms which may be utilized may include, e.g., optical flow estimation to compute an approximation to the motion field from time-varying image intensity. Additionally, methods for evaluating motion estimation may also include, e.g., correlation, block matching, feature tracking, energy-based algorithms, as well as, gradient-based approaches, among others.

In some cases, the image frames may be shifted by simple translation and/or rotation and may not contain a significant degree of distortion or other artifacts to greatly simplify the image processing methods and increase overall speed. Alternatively, the hardware and software system can also create a composite image that is comprised (or a combination) of multiple frames during a motion cycle by employing a variety of image stitching algorithms, also known in the art (see e.g., R. Szeliski. Image Alignment and Stitching. A Tutorial. *Handbook of Mathematical Models in Computer Vision.* (Editors: N. Paragios, et al.). Pages 273-292, 2005), which is incorporated herein by reference in its entirety. A graphical feature, e.g., a circle, square, dotted-lines, etc, can be superimposed or overlaid on the composite image in order to indicate the actual position of the camera (image) based on the information obtained from the image tracking software as the camera/hood undergoes a certain excursion, displacement, etc., relative to the target tissue of the organ structure.

An estimate of motion and pixel shifts may also be utilized. For example, a fibrillating heart can achieve 300 bpm (beats per minute), which equals 5 beats per second. Given a video capture rate of 30 fps (frames per second) there would then be roughly 6 frames captured during each beat. Given a typical displacement of, e.g., 1 cm of the camera/hood relative to the plane of the surface of the target tissue per beat, each image may record a displacement of about 1.6 mm per frame. With a field of view (FOV), e.g., of about 7 mm, then each frame may represent an image shift of about 23%. Given an image sensor size of, e.g., 220 pixels×224 pixels, the number of pixels displaced per frame is, e.g., 50 pixels.

Image processing and analysis algorithms may be extremely sensitive to instabilities in, e.g., image intensity, lighting conditions and to variability/instability in the lighting (or image intensity) over the sequence of image frames, as this can interfere with the analysis and/or interpretation of movement within the image. Therefore, mechanisms and methods of carefully controlling the consistency of the lighting conditions may be utilized for ensuring accurate and robust image analysis. Furthermore, mechanisms and methods for highlighting surface features, structures, textures, and/or roughness may also be utilized. For example, a plurality of peripheral light sources, e.g., from flexible light fiber(s), or individual light emitting diodes (LEDs) can create even symmetrical illumination or can be tailored to have one or all illuminating sources active or by activating sources near each other in order to provide focused lighting from one edge or possibly alternate the light sources in order to best represent, depict, characterize, highlight features of the tissue, etc. The light source can be configured such that all light sources are from one origin and of a given wavelength or the wavelength can be adjusted for each light element. Also, the light bundles can be used to multiplex the light to other different sources so that a given wavelength can be provided at one or more light sources and can be controlled to provide the best feature detection (illumination) and also to provide the most suitable image for feature detection or pattern matching.

As further described herein, light fibers can be located at the periphery of the hood or they can be configured within the hood member. The incidence angle can be tailored such that the reflected light is controlled to minimize glare and other lighting artifacts that could falsely appear as surface features of interest and therefore possibly interfere with the image tracking system. The lighting requirements that provide optimal visual views of the target tissue for the user may vary from the lighting requirements utilized by the software to effectively track features on the target tissue in an automated manner. The lighting conditions can be changed accordingly for different conditions (e.g., direct viewing by the user or under software control) and can be automatically (e.g., software controlled) or manually configurable. Lighting sources could include, e.g., light emitting diodes, lasers, incandescent lights, etc., with a broad spectrum from near-infrared (>650 nm) through the visible light spectrum.

As the camera actively tracks its position relative to the target tissue, the power delivered by the RF generator during ablation may also be controlled as a function of the position of the hood in order to deliver energy to the tissue at a consistent level. In situations where the excursions of the hood/camera occur with varying velocity, the power level may be increased during periods of rapid movements and/or decreased during periods of slower movements such that the average delivery of energy per region/area (per unit time) is roughly constant to minimize regions of incomplete or excessive ablation thus potentially reducing or eliminating damage to surrounding tissue, structures or organs. Alternatively, the tracking of the target tissue may be utilized such that only particular regions in the moving field receive energy whereas other areas in the field receive none (or relatively less energy) by modulating the output power accordingly by effectively gating the power delivery to a location(s) on the target tissue. This technique could ultimately provide higher specificity and focal delivery of ablative energy despite a moving RF electrode system relative to the target tissue.

Active or dynamic control of the hood using control wires, etc., may also be used in order to match/synchronize the excursion of the device with that of the tissue by utilizing surface sensors and/or optical video image to provide feedback to motion control.

Figure 6A:
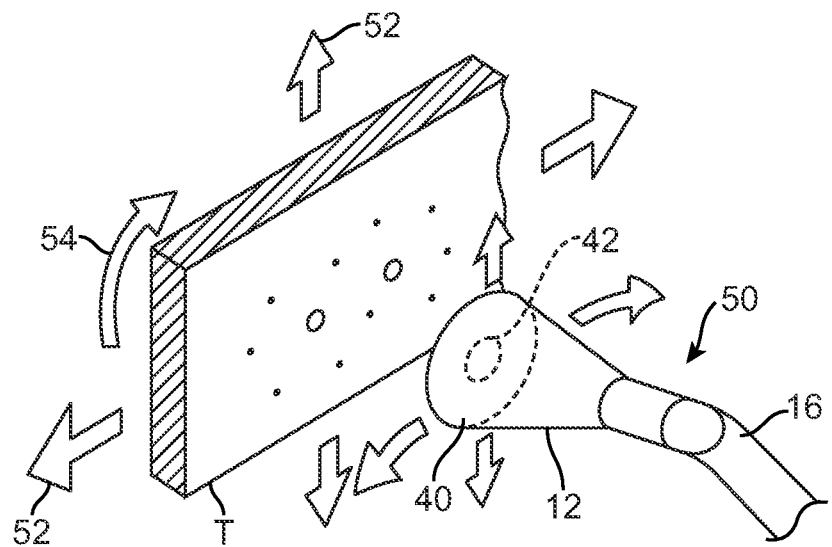
FIGS. 6A and 6B show perspective views of a targeted tissue region which is actively moving and a visualization assembly which is positioned against the tissue while also moving in a corresponding manner to effect a stable image of the moving tissue.

Turning now to FIG. 6A, a perspective view of a typical section of target tissue T from an organ that is actively moving, either due to contractility (such as in a heart), respiration, peristalsis, or other tissue motion, as depicted by arrows in the plane of the tissue, which can include lateral tissue movement 52 or rotational tissue movement 54. The target tissue T can also experience displacement along an axis normal to the plane of the tissue. The hood 12 of the visualization assembly may be seen in proximity to the tissue region T where the hood 12 may be positioned upon an articulatable section 50 of the catheter 16.

Figure 6B:
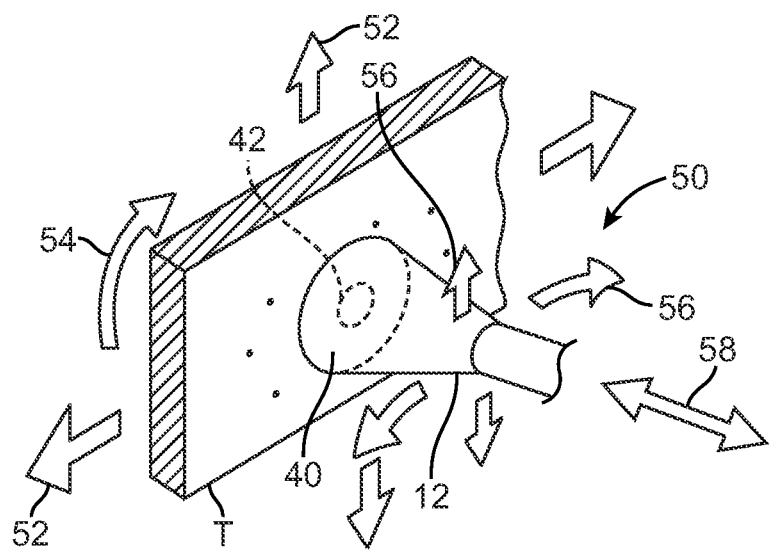

As shown in the perspective view of FIG. 6B, any movement of the underlying tissue region T may be matched by the catheter assembly by moving the hood 12 in a manner which corresponds to the movement of the tissue T. For instance, any axial displacement 58 of the hood 12 corresponding to any out-of-plane movement of the tissue region T may be achieved by advancing and retracting the catheter 16. Similarly, any corresponding lateral catheter movement 56 of the hood 12 may be accomplished by articulating the steerable section 50 the catheter 16 to match correspondingly to the lateral movements 52 of the tissue T. Steerable section 50 may be manually articulated to match movements of the hood 12 with that of the tissue. Alternatively, computer control of the steerable section 50 may be utilized to move the hood 12 accordingly. Examples of steering and control mechanisms which may be utilized with the devices and methods disclosed herein may be seen in U.S. patent application Ser. No. 11/848, 429 filed Aug. 31, 2007 (U.S. Pub. 2008/0097476) which shows and describes computer-controlled articulation and steering. Other examples include U.S. patent application Ser. No. 12/108,812 filed Apr. 24, 2008 (U.S. Pub. 2008/0275300) which shows and describes multiple independently articulatable sections; U.S. patent application Ser. No. 12/117,655 filed May 8, 2008 (U.S. Pub. 2008/0281293) which shows and describes alternative steering mechanisms; U.S. patent application Ser. No. 12/499,011 filed Jul. 7, 2009 (U.S. Pub. 2010/0004633); and Ser. No. 12/967,288 filed Dec. 14, 2010 which show and describe steering control mechanisms and handles. Each of these references are incorporated herein by reference in its entirety.

Figure 7:
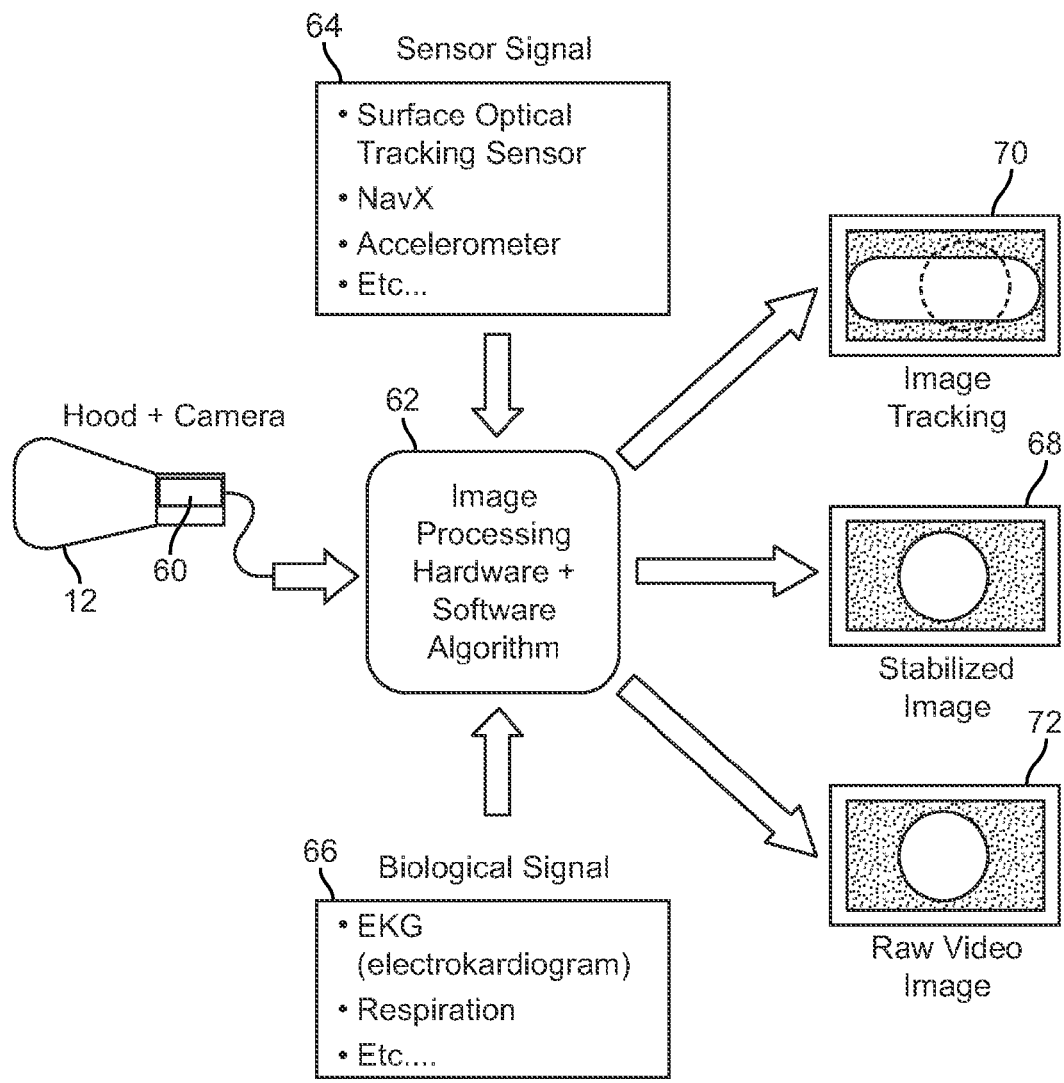
FIG. 7 illustrates a schematic diagram that represents an example of how the imaging output captured from the imager may be transmitted to a processor for processing the captured images as well as other data.

FIG. 7 illustrates a schematic diagram that represents an example of how the imaging output captured from the imager 60 (as described above) within or adjacent to the hood 12 may be transmitted to a processor 62 that may comprise imaging processing hardware as well as software algorithms for processing the captured images as well as other data. For instance, processor 62 may also receive signals from one or more sensors 64 located along or in proximity to the hood 12 which sense and detect positional information of the hood 12 and/or catheter 16. Such sensors may include, e.g., surface optical tracking sensors, positional information received from a NavX® system, Carto® Navigation System (Biosense Webster, Calif.), accelerometers, etc. Processor 62 may also receive biological signals or physiological data 66 detected by one or more sensors also located along or in proximity to the hood 12 or from other internal or external inputs, e.g., electrocardiogram data, respiration, etc.

With the processor 62 programmed to receive and process both the positional information from one or more sensor signals 64 as well as physiological information of the subject from one or more biological signals 66, the processor 62 may optionally display one or more types of images. For example, a composite image 70 may be processed and displayed where the image represents a composite image that is combined, stitched-together, or comprised of multiple images taken over the excursion distance captured by the imager 60 during relative movement between the tissue and hood 12. Additionally and/or alternatively, a stabilized composite image 68 may be displayed which represents an image where the motion due to tissue displacement is reduced, minimized, or eliminated and a single view of an "average" image. Additionally and/or alternatively, a raw video image 72 may be displayed as well which shows the unprocessed image captured by the imager 60. Each of these different types of images may be displayed individually or simultaneously on different screens or different portions of a screen if so desired.

Figure 8:
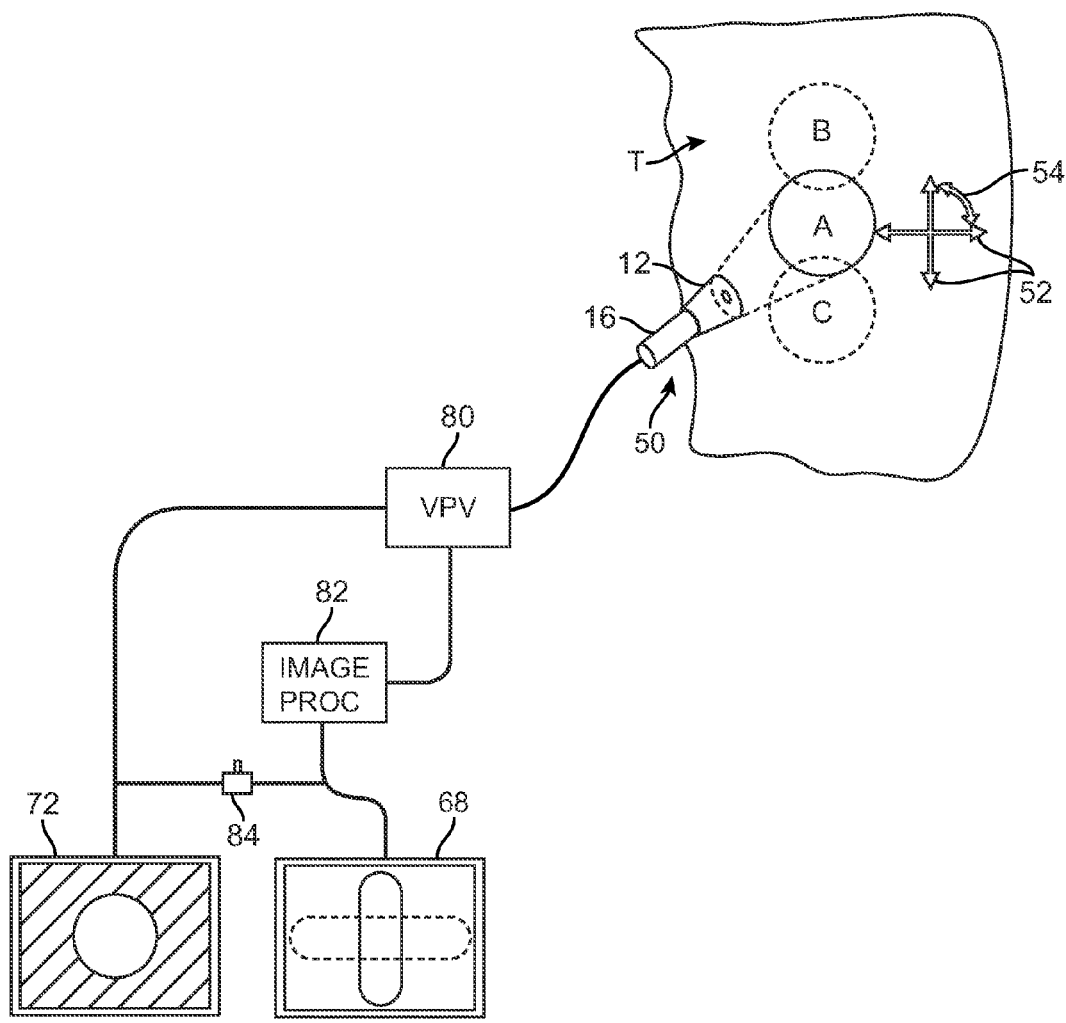
FIG. 8 shows a representative view of a visualization assembly electronically coupled to a video processing unit and an optional image processing unit for providing multiple images of the tissue region.

FIG. 8 depicts the hood 12 and catheter 16 imaging a tissue region T which may undergo tissue displacement, e.g., within three degrees of freedom (linear displacements 52 and rotational displacement 54). The captured images may be transmitted to a video processing unit 80 (VPU) which may process the raw video images 72 for display upon a monitor. The VPU 80 may further transmit its images to an image processing unit 82 which may contain the processor 62 and algorithm for stabilizing and/or stitching together a composite image. The stabilized composite or averaged image 68 captured from tissue regions A, B, C during tissue movement can be viewed on a second monitor. Optionally, the processing function of image processing unit 82 can also be turned off or toggled, e.g., via a switch 84, for use on one or more monitors to enable the physician to select the type of image for viewing. Additionally, although a typical target tissue T is described, the imaging angle of the tissue may change relative to the hood 12 during image capture of the tissue region T due to the relative tissue movement. Because of this changing image, images of the tissue T at various stages at a particular given time interval may be displayed if so desired for comparison.

Figure 9:
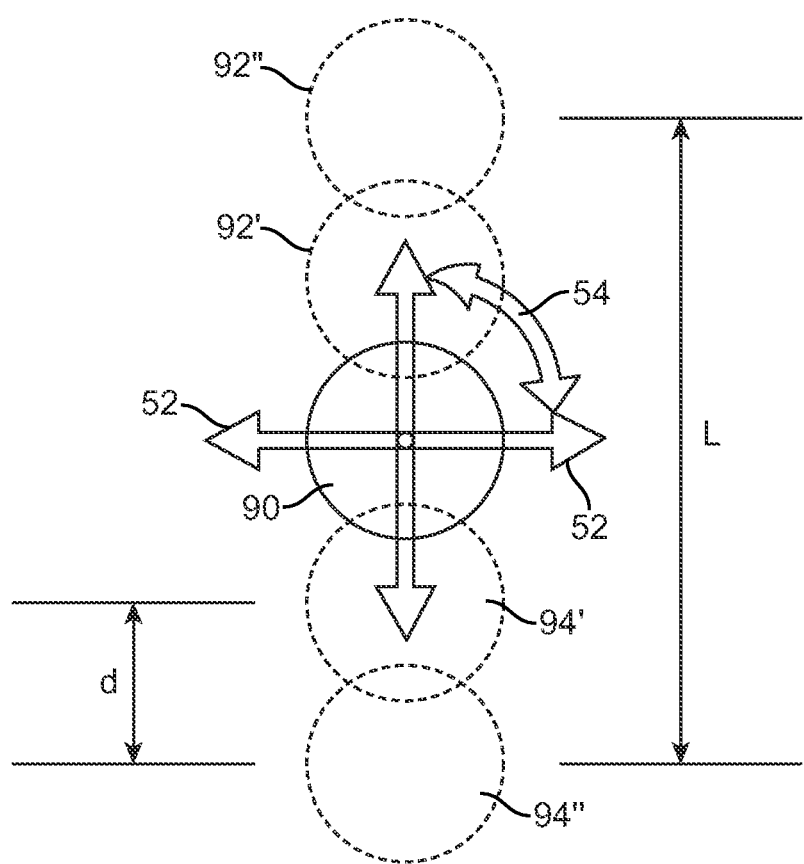
FIG. 9 depicts a series of images which may be captured during a total excursion of the tissue displacement of the hood relative to the moving tissue.

As an example of the range of images the imager within or adjacent to the hood 12 may capture during relative tissue movement, FIG. 9 depicts a series of images which may be captured during the total excursion L of the tissue displacement of the hood 12 relative to the moving tissue. The image represented by the static field of view 90 through hood 12 shows an initial position of hood 12 relative to the tissue. As the tissue moves relative to the hood 12, the sampling rate or frame rate of the imager may be sufficiently high enough such that as the tissue moves relative to the hood, each subsequent imaged tissue regions in a first direction 92', 92" may be captured at increments of a distance d which may allow for overlapping regions of the tissue to be captured. Likewise, the imaged tissue regions in a second direction 94', 94" may be captured as well at overlapping increments of distance d between each captured image.

Figure 10A:
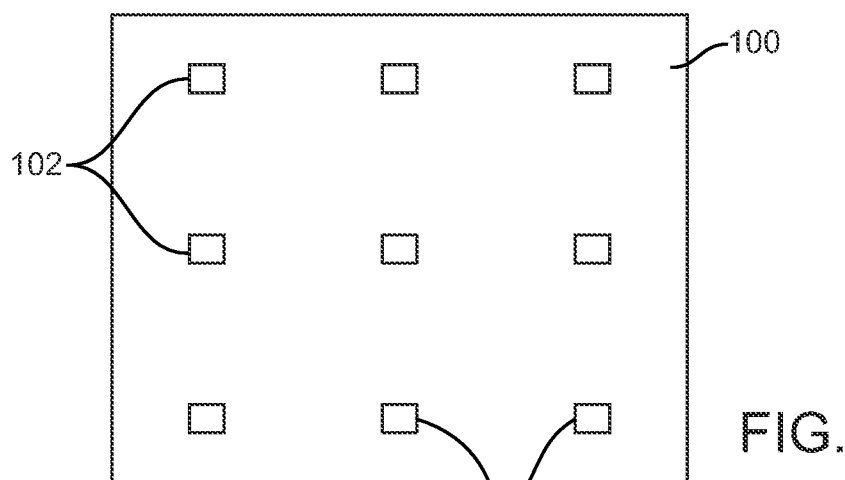
FIG. 10A shows an example of how an entire video image taken by the imager may be processed to identify one or more sub-sample regions at discrete locations.
Figure 10B:
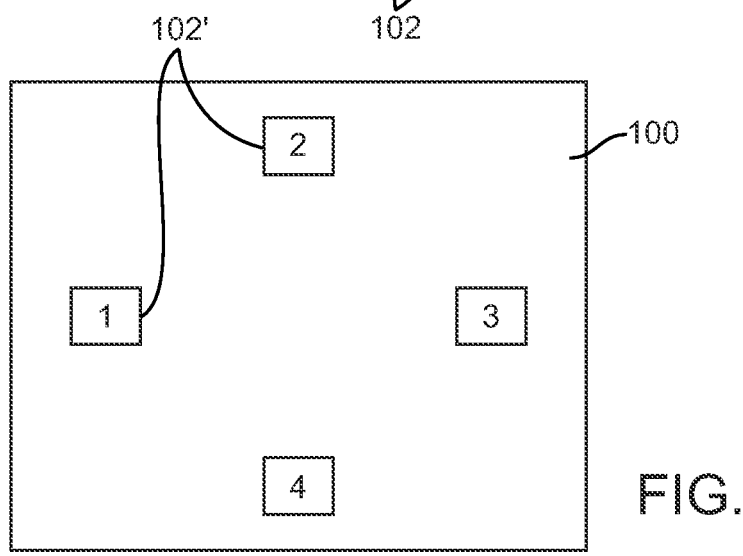
FIGS. 10B and 10C show examples of how the identified sub-sample regions may be located in various patterns.
Figure 10C:
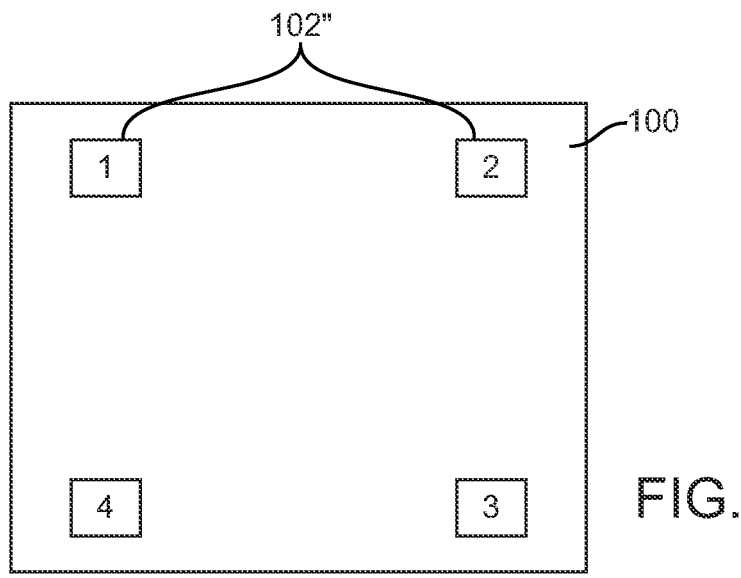

In processing the captured images to provide a stabilized or composite tissue image for display, one example is illustrated in FIG. 10A which shows an example of how an entire video image 100 (e.g., 220×224) can be taken by the imager and then processed by the processor 62 to identify one or more sub-sample regions 102 (e.g., 10×10 pixel subsets up to 18×18 pixel subsets) at discrete locations. These identified sub-sample regions 102 may be identified consistently between each subsequent image taken for mapping and/or stitching purposes between the subsequent images. The sub-sample regions 102 may range between, e.g., 1-20 subsets, and may be oriented in various patterns to best match or be removed from obstructions (e.g., various hood features, etc.) for the most robust image quality and processing. FIG. 10B shows an example of how the identified sub-sample regions 102' may be located in a first staggered pattern while FIG. 10C shows another example of how the sub-sampled regions 102" can be identified along the corners of the image 100. The location of the sub-sampled regions are illustrated for exemplary purposes and other locations over the image 100 may be identified as needed or desired.

Figure 11:
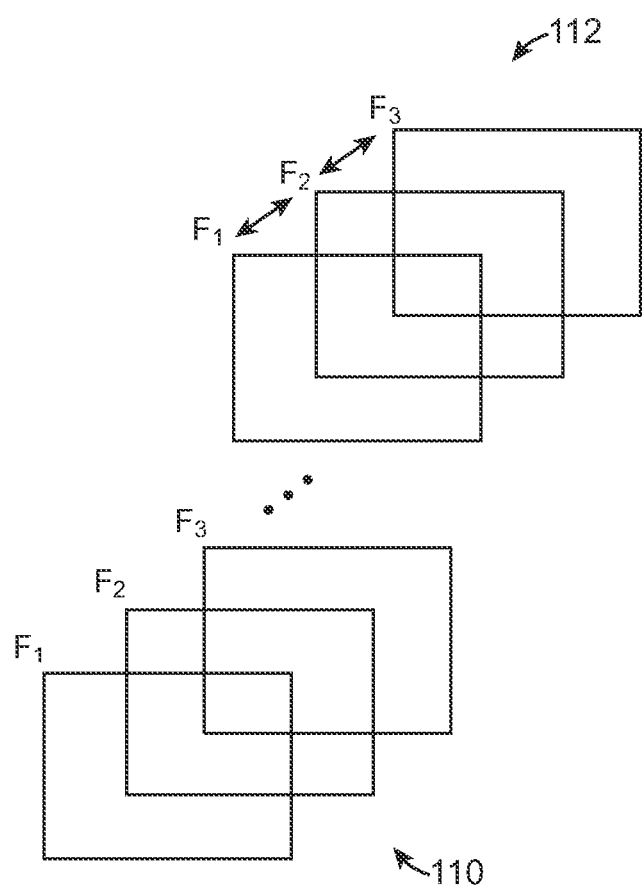
FIG. 11 illustrates how multiple captured images of the underlying tissue region may overlap when taken while the tissue moves relative to the hood over a predetermined time sequence.

With the sub-sample regions identified, FIG. 11 depicts how the multiple captured images 110 (e.g., F1, F2, F3, etc.) of the underlying tissue region may overlap when taken while the tissue moves relative to the hood 12, e.g., at 1 cm increments, over a predetermined time sequence. Subsequent images may be automatically compared 112 by the processor 62 for comparison from one image to the other utilizing the identified sub-sample regions between each image. An example of such a comparison between two subsequent images is shown, e.g., between frame F1 to frame F2 and between frame F2 and frame F3, etc. In this manner, multiple images may be compared between each sampled frame.

Figure 12:
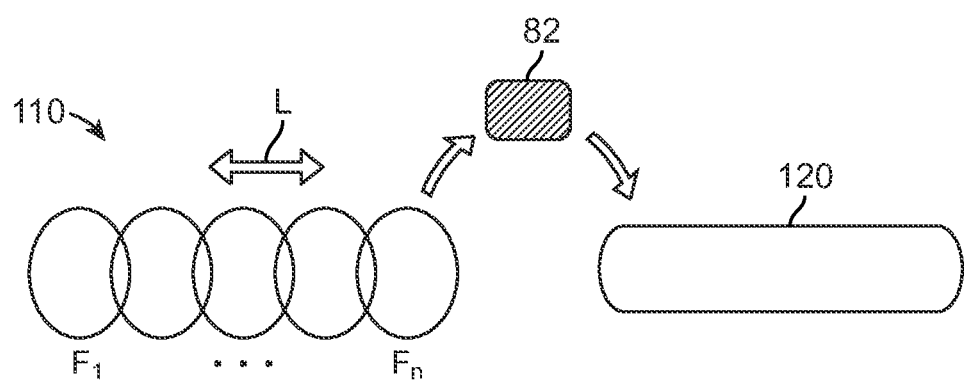
FIG. 12 illustrates multiple images captured over an excursion length relative to the tissue region and processed to create a composite image.
Figure 13:
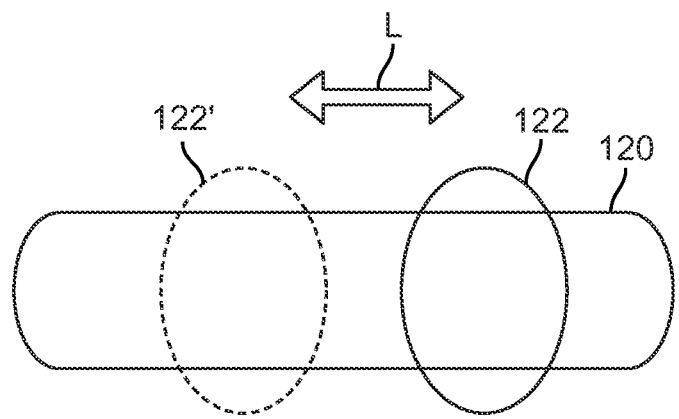
FIG. 13 illustrates how a graphical feature such as a positional indicator can be superimposed over the composite image.

Another example is shown in FIG. 12 depicting multiple images (e.g., F1 to Fn) which are captured over an excursion length L of the hood 12 relative to the tissue region. While the images are captured and tracked over a time period, the imaging processing unit 82 may receive these multiple images and process the images to create a composite image 120 stitched from each individual captured frame in order to simplify viewing by the user. With this composite image 120, which can be continuously updated and maintained as the tissue T and/or hood 12 moves relative to one another, a graphical feature such as a positional indicator 122, e.g. a circle, can be superimposed over the composite image 120 at a first location for display to the user to depict the actual position of the hood 12 in real time relative to the tissue T, as shown in FIG. 13. Positional indicator 122' is also illustrated at a second location along the tissue T. Use of the positional indicator for display may be incorporated to depict where the hood 12 is in real time relative to the tissue T, or more specifically, where hood 12 is relative to anatomical markers or features of interest, especially when using ablation energy.

Figure 14:
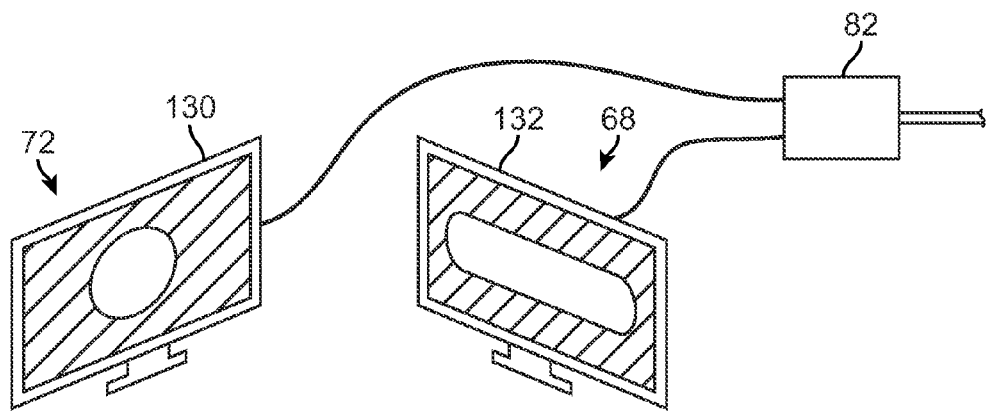
FIG. 14 illustrate an example of how the tissue image may be displayed in alternative ways such as the unprocessed image on a first monitor and the stabilized composite image on a second optional monitor.
Figure 15A:
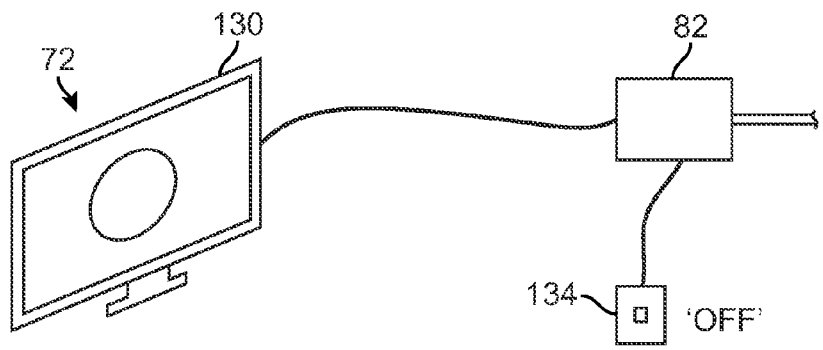
FIGS. 15A and 15B show examples of alternative views of the tissue images which may be toggled via a switch on a single monitor.
Figure 15B:
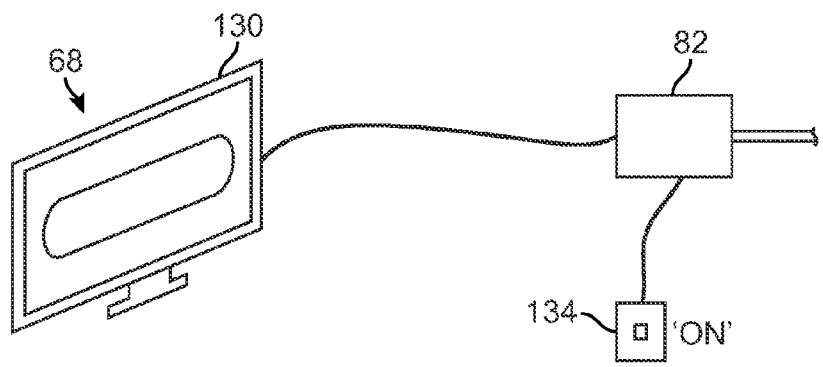

As previously described and as shown in FIG. 14, the tissue image may be displayed in alternative ways, such as the unprocessed image 72 on a first monitor 130 and the stabilized composite image 68 on a second optional monitor 132. Alternatively, a single monitor 130 may be used with a switch 134 electrically coupled to the imaging processing unit 82. Switch 134 may allow the user to compare one image with the other and decide which one is best suited for the task at hand, e.g., gaining access to the target region, exploring within the target region, or to stabilize and track the target tissue in order to commence with ablation or other therapy. Thus, the user may use the switch 134 to toggle between the unprocessed image view 72, as shown in FIG. 15A, and the stabilized composite image 68 on a single monitor 130, as shown in FIG. 15B.

Figure 16A:
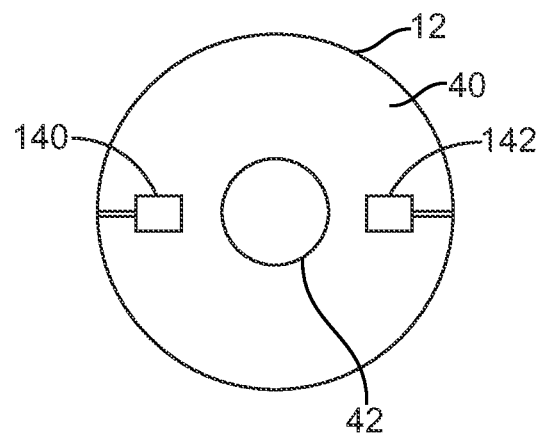
FIGS. 16A and 16B show examples of end views of the hood having multiple sensors positioned upon the membrane.
Figure 16B:
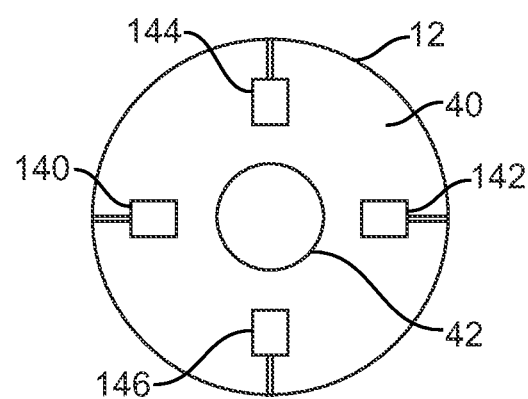

In an alternative variation, rather than using the imager within or adjacent to the hood 12 for tracking and sampling the images of the underlying tissue, one or more individual sensors (as previously mentioned) may be positioned along or upon the hood 12 such as along the membrane 40 in proximity to aperture 42. As shown in the end view of hood 12 in FIG. 16A, a first optical displacement sensor 140 is shown positioned upon membrane 40 with a second sensor 142 positioned on an opposite side of membrane 40 relative to first sensor 140. Another variation is shown in the end view of FIG. 16B which shows membrane 40 with the addition of a third sensor 144 and fourth sensor 146 positioned along membrane 40 uniformly relative to one another around aperture 42. In other variations, a single sensor may be used or any number of sensors greater than one may be utilized as practicable.

In use, multiple sensors may provide for multiple readings to increase the accuracy of the sensors and the displacements of the hood 12 may be directly tracked with the sensor-based modality like an optical displacement sensor such as those found in optical computer mice directly mounted to the face of the hood 12 (or some feature/portion of the hood 12). Additional sensors may be able to provide a more robust reading, especially if one sensor is reading incorrectly due to poor contact or interference from blood. Because the hood 12 is deformable, the relative position of each sensor relative to each other may be independent of one another, thus, the detected values may be averaged or any accumulated errors may be limited.

Figure 17A:
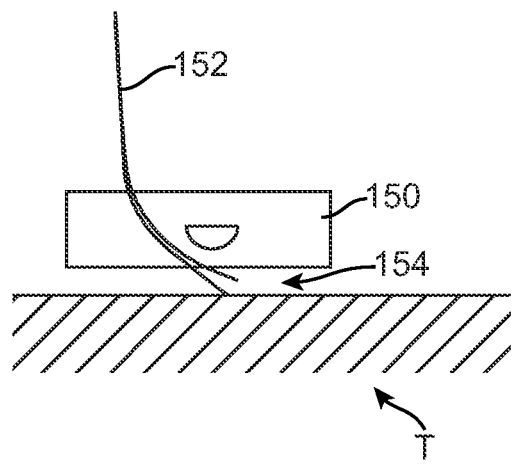
FIGS. 17A and 17B show partial cross-sectional side views of examples of an optical tracking sensor which may be positioned upon the hood.
Figure 17B:
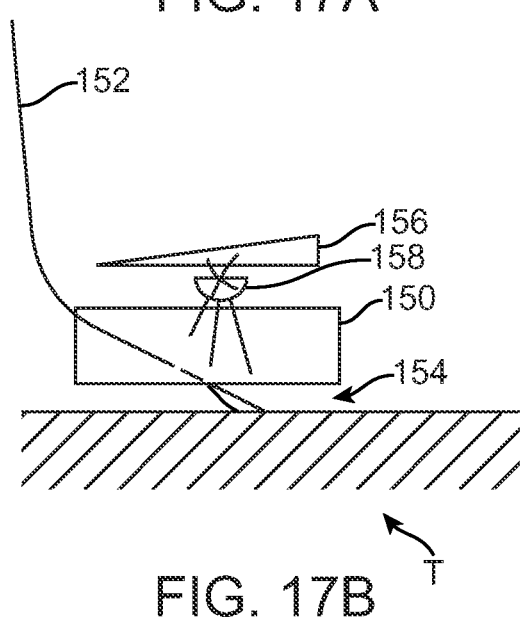

FIG. 17A shows a partial cross-sectional side view of one example of an optical tracking sensor 150 which may be positioned upon the hood 12 as described above. Sensor 150 may generally comprise a light source such as an optical fiber 152 optically coupled to a light source and having a distal end which may be angled with respect to the sensor 150 from which transmitted light 154 may be emitted such that the transmitted light 154 is incident upon the tissue T at an angle to create a side-lighting effect which may highlight or exaggerate surface features. FIG. 17B shows a partial cross-sectional side view of another variation where sensor 150 may also include a detector 156 having various sizes (e.g., 16×16 pixels, 18×18 pixels, or any other detector size) as well as a lens 158. Moreover, although a single optical fiber 152 is shown, multiple fibers may be utilized in other variations.

Figure 18A:
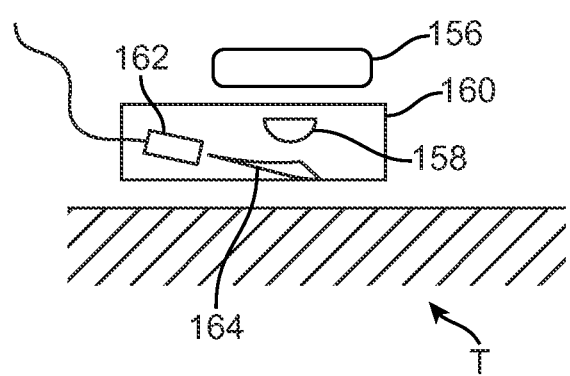
FIGS. 18A and 18B show partial cross-sectional side views of another example of an optical tracking sensor having integrated light sources for tracking the tissue images.
Figure 18B:
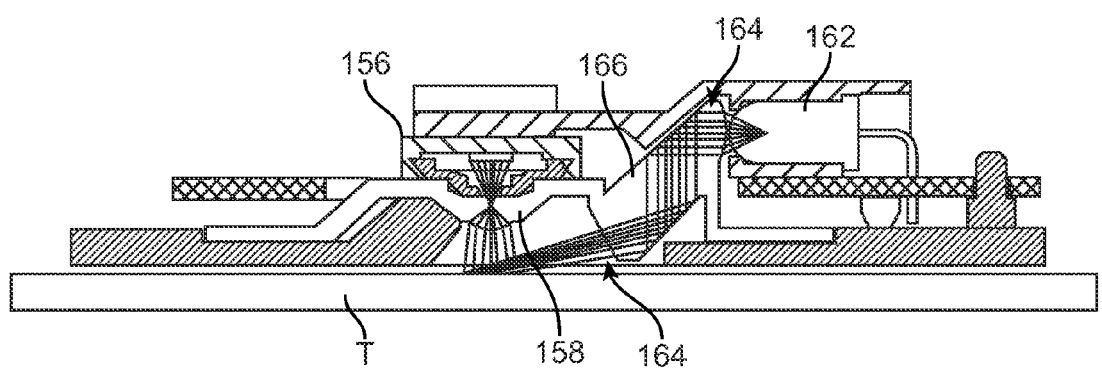

FIG. 18A shows a cross-sectional side view of another variation of an optical displacement sensor 160 having an integrated light source 162, e.g., light emitting diode (LED), laser, etc., rather than using a light source removed from the sensor 160. The integrated light source 162 may be angled (or angled via a lens or reflector) such that the emitted light 164 incident upon the tissue T emerges at an angle relative to the tissue surface. An example of an integrated light source 162 (such as an LED) similar to a configuration of an optical mouse sensor is shown in the cross-sectional side view of FIG. 18B for integration into sensor 160. As shown, the integrated light source 162 may be positioned within the sensor and a light pipe 166 may be positioned in proximity to the light source 162 to direct the emitted light through the sensor such that the emitted light 164 emerge at an angle with respect to the imaged tissue T to highlight/exaggerate surface features. The light reflected from the tissue may be reflected through lens 158 which may direct the reflected light onto detector 156. The detected image may then be transmitted to the processor 62, as previously described.

Figure 19A:
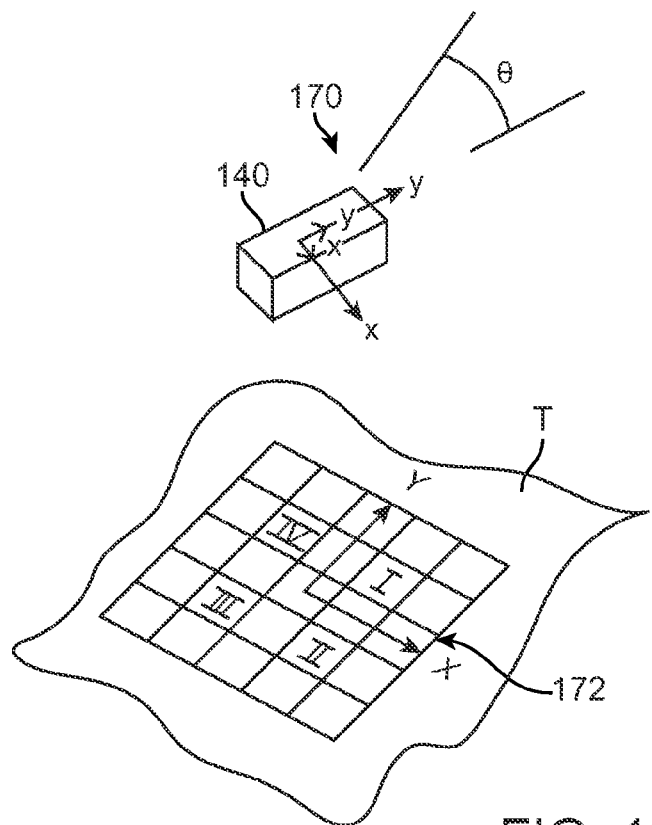
FIGS. 19A and 19B illustrate representations of a local coordinate system provided by the sensor and a global coordinate system relative to the tissue region of interest.

With respect to the use of one or more positional sensors, such sensors may be mounted upon or along the hood 12 and/or catheter 16 to calculate a position of the hood 12. Additional examples of positional sensors which may be utilized with the systems and methods described herein are shown and described in further detail in U.S. patent application Ser. No. 11/848,532 filed Aug. 31, 2007 (U.S. Pub. 2009/0054803), which is incorporated herein by reference in its entirety. An example is shown FIG. 19A which illustrates a representation of a local coordinate system 170 for providing three degrees-of-freedom (e.g., x, y, θ) and a global coordinate system 172 referenced with respect to a predetermined grid, marker, pattern, etc. such as from tissue fiber images, tissue texture, etc. The sensor 140 positioned upon or along the hood 12 and/or catheter 16 may provide for proper sensing via local information generated relative to the sensor 140 itself (rather than global information) which may be calculated such that in the event the tracking is lost, the system can simply wait for a subsequent cardiac cycle (or tissue movement) to recalculate the excursion again as the tracking would only be active when the image is stabilized and the catheter control is well maintained. The local coordinate system 174 may for provide two degrees-of-freedom (e.g., x, y) referenced within the sensor 140 since the light source and sensing occurs from the same reference point.

Figure 19B:
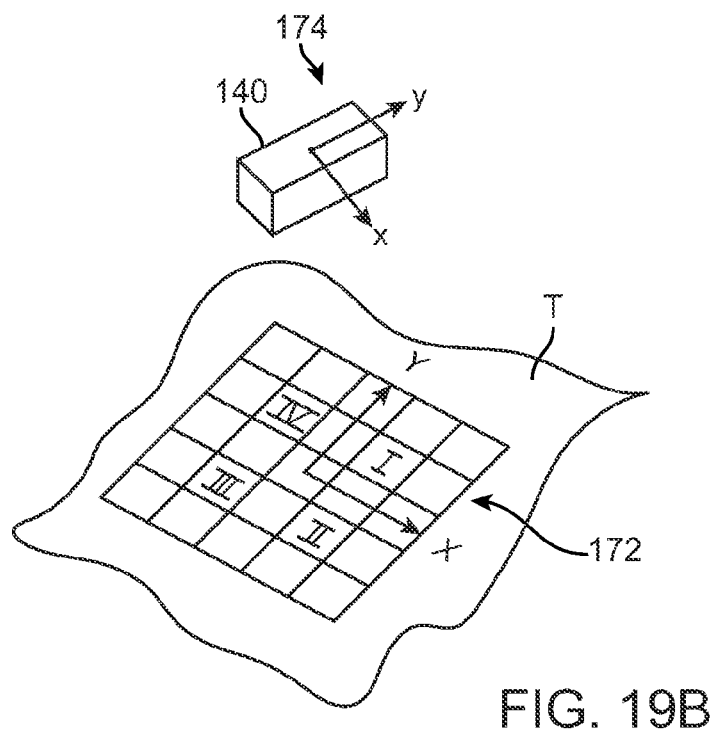

Alternatively, the global coordinate system 172 may be utilized relative to the tissue region. If imaging of the tissue surface does not provide sufficient "markers" to track then alternative methods of providing fiducial markers may be utilized, e.g., sensor may calculate axial displacements (two degrees-of-freedom) and possibly at least one rotational degree-of-freedom to provide a rotational component. FIG. 19B shows another variation where only axial displacements are detected to provide a more robust sensing due to the relatively fewer pixel representations of the surface.

Figure 20:
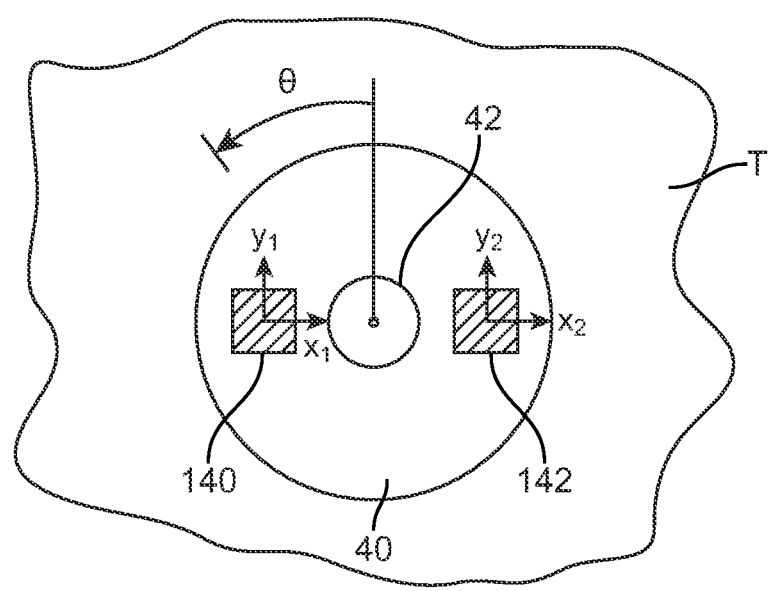
FIG. 20 shows an end view of an example of sensors which may be positioned along the hood over or upon the membrane for providing an estimated average of tissue displacement.

An example of sensors 140, 142 which may be positioned along the hood 12 over or upon the membrane 40 in proximity to aperture 42 is shown in the end view of FIG. 20. These positional sensors 140, 142 may be independent or integrated with the sensors used for imaging. As shown, the one or more sensors may be used individually for detecting a linear translation of the hood 12 where the displacement of the entire hood 12 may be estimated based upon an averaging of the translation of each individual sensor where $(y_1+y_2)/2=y_{hood}$ and $(x_1+x_2)/2=x_{hood}$. An angle of rotation may also be estimated by utilizing the rotation of each individual sensor where the overall rotation of the hood 12 is a function of the displacements of each sensor 140, 142. In this example, the overall estimated rotation of the hood, $\Theta_{hood}=f([x1, y1], [x2, y2])$ and the overall displacement may be determined as an average between the displacements of each sensor 140, 142 where $y_{hood}=(y_1+y_2)/2$ and $x_{hood}=(x_1+x_2)/2$. The use of the two sensors is illustrated as an example and more than two sensors may optionally be utilized. Moreover, the positioning of the sensors may be varied as well and are not limited to positioning upon the membrane 40.

Figure 21:
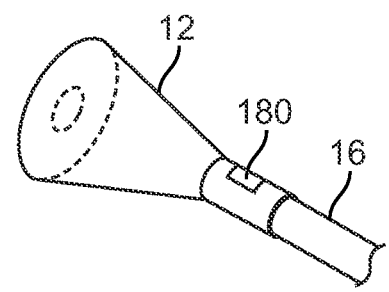
FIG. 21 shows another variation where an accelerometer may be mounted to the hood or along the catheter.
Figure 21:
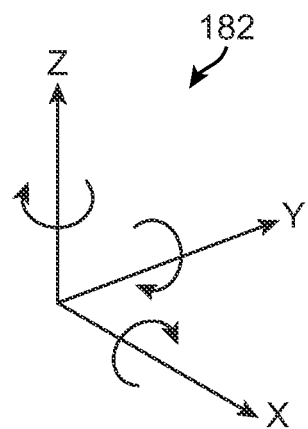

FIG. 21 shows another variation where an accelerometer 180 may be mounted to the hood 12 or along catheter 16 and may be used to provide a mechanism of gating or timing the excursions or at least the change in directions of detected movements 182. This variation may be incorporated as another input to the tracking algorithm by the processor.

Turning back to the emission of an angled light incident upon the tissue surface, as previously mentioned the emitted light for surface detection may be angled relative to the sensor as well as relative to the tissue. An example is illustrated in the representative assembly of FIG. 22A, which shows an optical fiber 152 positioned at an angle such that the emitted light 154 is incident upon the tissue T at an angle, Θ. The angled light may illuminate surface features or details along the tissue surface that can be used for tracking. Low-angled (relative to the surface) side lighting provided by optical fiber 152 coupled to light source 194 may be used or an LED, laser, or other lighting elements could also be utilized along the hood 12 in proximity to the tissue surface to achieve similar low angled lighting to provide improved detail to small surface features. Alternately, the light source can be comprised of one or more LEDs mounted directly on or in the hood. The reflected light may be captured within the field of view 192 of imaging element 190 positioned within or adjacent to hood 12, as shown.

FIG. 22B shows a variation where direct axial illumination, as shown, may be used where one or more optical fibers 152, LEDs, or other light source may be positioned so as to emit light axially relative to the imaging element 190. In this variation, the light is incident upon the tissue surface perpendicularly. FIG. 22C depicts another variation where a shallower angle of illumination can help highlight the features of the tissue surface in the captured images. FIG. 22D also illustrates another variation where multiple light sources 150, 150' may be used for emitting light 154, 154' at multiple angled positions for depicting tissue surface features at multiple angles.

Figure 23A:
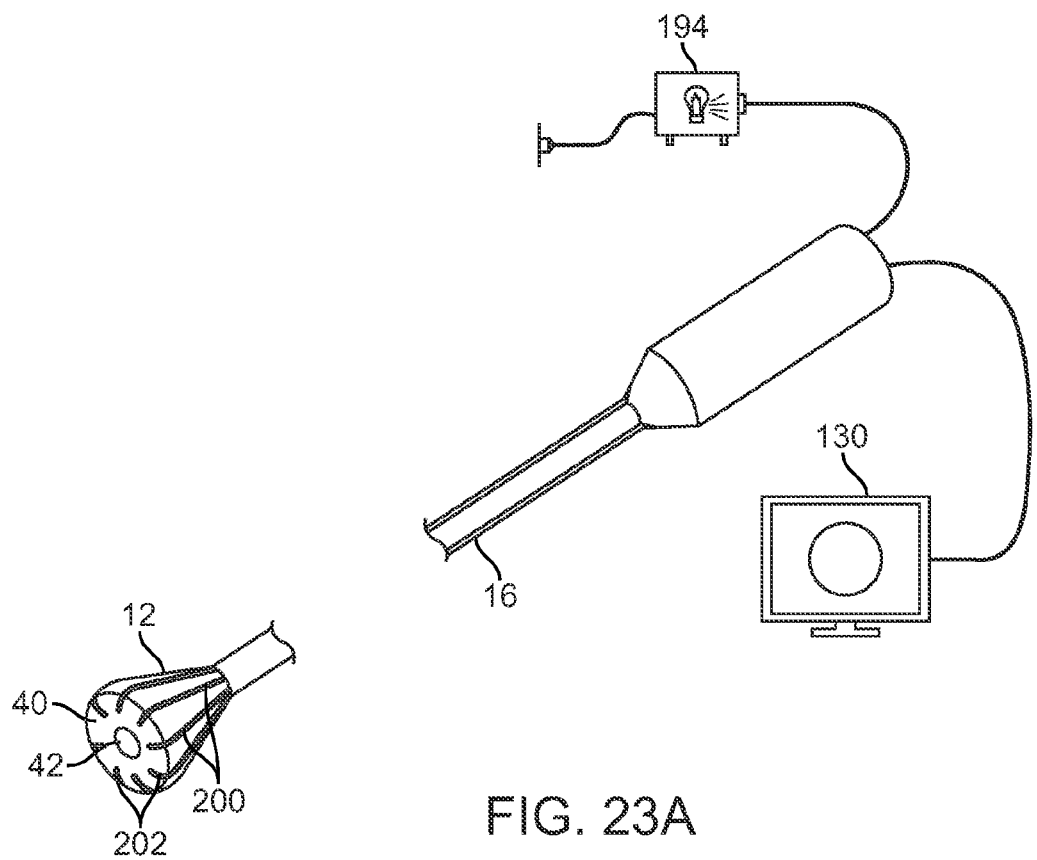
FIGS. 23A and 23B show perspective assembly and end views, respectively, of a hood having multiple optical fibers positioned longitudinally along the hood to provide for angled lighting of the underlying tissue surface from multiple points of emitted light.
Figure 23B:
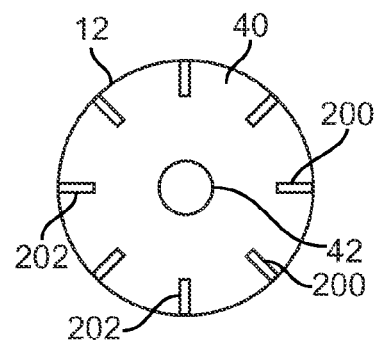

FIG. 23A shows a perspective view of an assembly having a hood 12 with multiple optical fibers positioned longitudinally along the hood to provide for angled lighting of the underlying tissue surface from multiple points of emitted light. As illustrated also in the end view of hood 12 in FIG. 23B, the terminal emitting ends 202 of multiple optical fibers 200 (which may be each optically coupled to a common light source 194 or each individually to separate light sources) may be positioned circumferentially around the hood 12 such that the ends 202 are directed towards the aperture 42. In this manner, the emitted light may converge on the aperture 42 (or any region of the tissue surface being visualized) to provide shallow angle edge lighting. The number of fibers can range anywhere from, e.g., 1 to 50 or more, and can be symmetrically or asymmetrically distribute about the hood face. Alternatively, optical fibers 200 may be replaced by individual LEDs.

Figure 24A:
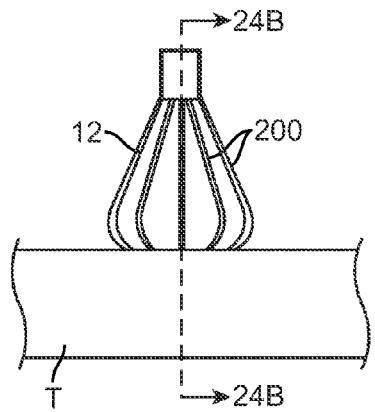
FIGS. 24A and 24B side and cross-sectional side views of the hood with a plurality of light fibers illuminating the surface of the target tissue.
Figure 24B:
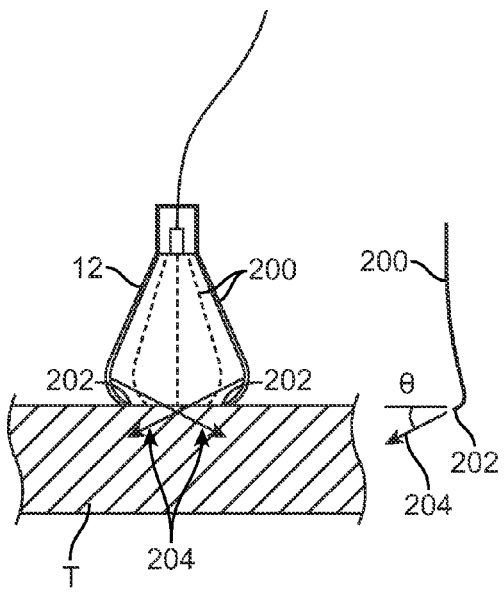

FIG. 24A illustrates a side view of hood 12 with a plurality of light fibers 200 on the surface of the target tissue T and FIG. 24B shows a cross-sectional side view of FIG. 24A illustrating the illumination angle, Θ, of the incident light 204 which may penetrate the tissue T to a certain depth depending on the light intensity and wavelength.

Figure 25A:
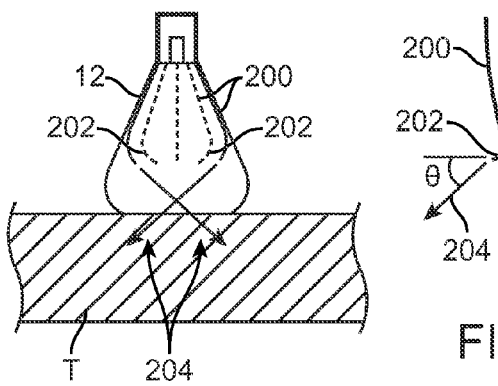
FIGS. 25A and 25B show examples of light fibers having its ends further retracted for providing another lighting angle.
Figure 25B:
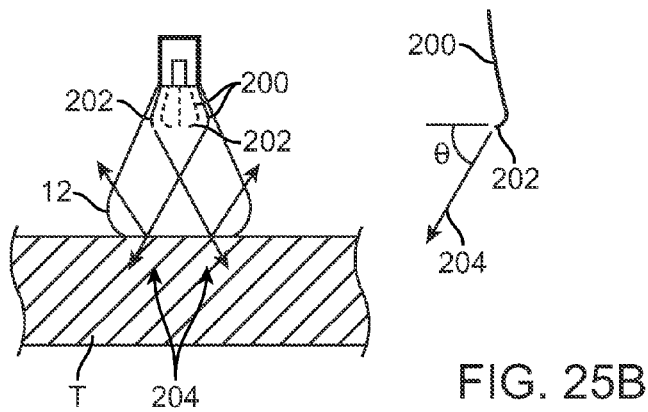

Another variation is shown in the cross-sectional side view of FIG. 25A showing optical fibers 200, LEDs, or other light sources along hood 12 with a relatively more retracted position of its ends 202 relative to the tissue surface to provide an alternative lighting scheme and to also enable to the light fibers to be shorter and not be subjected to the sharp bend and motion of the hood edge. As shown, the light fiber may have a relatively shallower tip angle, Θ, to redirect the light inward. FIG. 25B similarly depicts a hood 12 with light fibers 200 having its ends 202 which are further retracted for providing another lighting angle, Θ, as well as providing shorter light fibers that may be less prone to damage during hood manipulation or repeated deployments and retraction from within the delivery sheath.

Figure 26:
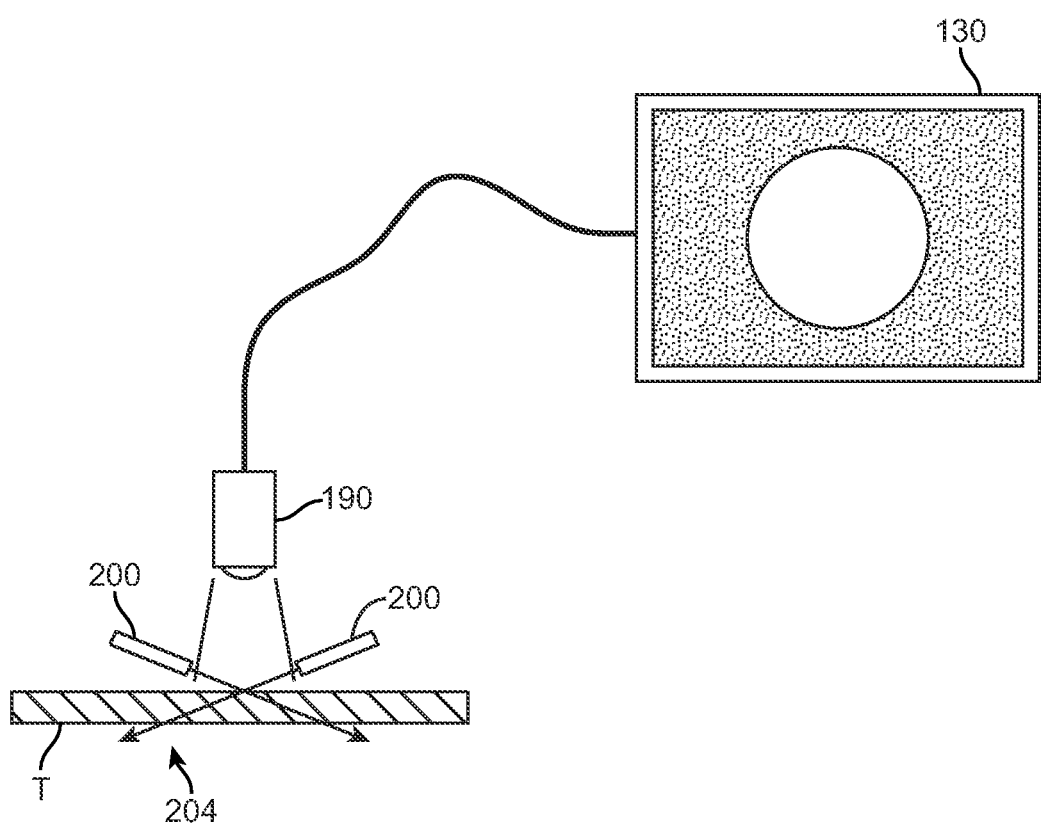
FIG. 26 shows illustrates yet another variation where a dark-field optical pathway may be created which highlights surface features of tissue but keeps the background relatively dark.

FIG. 26 illustrates yet another variation where a dark-field optical pathway may be created which highlights surface features of tissue T but keeps the background relatively dark. Segmentation of the image may be effected to provide better detail in the raw image for further processing rather than trying to process an image (using thresholding, segmenting, etc.) with poorly defined detail and features. Typically, a higher quality image can be easier to process rather than applying powerful image processing algorithms to a poor quality image. In particular, the substrate may be relatively translucent or dark. In the case of tissue, it may be that the incident light spectrum can "penetrate" the tissue with little reflection and scatter, yet help highlight surface features or texture. This may be utilized with relatively thin or somewhat translucent tissue types or thin membranes.

The applications of the disclosed invention discussed above are not limited to certain treatments or regions of the body, but may include any number of other applications as well. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

The invention claimed is:

1. A method for imaging a tissue region in motion, comprising:
   intravascularly advancing a deployment catheter towards the tissue region;
   expanding a non-inflatable barrier or membrane defining an open area and projecting distally from the deployment catheter against the tissue region;
   purging the tissue region of blood contained within the open area via a transparent fluid while the tissue region is moving, wherein the open area is in fluid communication through an opening with a blood-filled environment external to the barrier or membrane;
   visualizing the tissue region via a visualization element through the transparent fluid;
   sensing a displacement of the barrier or membrane relative to the tissue region with a plurality of sensors during tissue movement;
   capturing via the visualization element a plurality of images of a tissue region over a plurality of corresponding time intervals while the tissue region is moving; and,
   displaying a composite image of the plurality of images.

2. The method of claim 1 wherein purging comprises introducing saline through the deployment catheter.

3. The method of claim 1 wherein sensing a displacement comprises detecting lateral and/or rotational tissue movement relative to the barrier or membrane.

4. The method of claim 1 wherein capturing via the visualization element comprises imaging the tissue region via an electronic imager positioned within or adjacent to the open area.

5. The method of claim 1 wherein capturing via the visualization element comprises receiving positional data of the barrier or membrane from one or more sensors.

6. The method of claim 1 further comprising receiving physiological data of a subject while capturing the plurality of images.

7. The method of claim 1 wherein displaying a composite image comprises displaying an image stitched from the plurality of images captured during movement of the barrier or membrane relative to the tissue region.

8. The method of claim 7 further comprising displaying a stabilized image of the tissue region averaged from the plurality of images.

9. The method of claim 1 further comprising superimposing a graphical feature upon the composite image where the graphical feature is indicative of a position of the barrier or membrane relative to the tissue region.

10. The method of claim 1 wherein capturing a plurality of images comprises illuminating the tissue region via at least one light source angled with respect to the tissue region.

* * * * *